US009745586B2

(12) United States Patent
Bowser et al.

(10) Patent No.: US 9,745,586 B2
(45) Date of Patent: Aug. 29, 2017

(54) THERAPEUTIC POLYNUCLEOTIDES, COMPOSITIONS, AND METHODS

(71) Applicant: Regents of the University of Minnesota, Minneapolis, MN (US)

(72) Inventors: Michael T. Bowser, Inver Grove Heights, MN (US); Gianluigi Veglia, Minneapolis, MN (US); Meng Jing, Minneapolis, MN (US); Raffaello Verardi, Minneapolis, MN (US); Joseph M. Metzger, St. Paul, MN (US); Brian Raymond Thompson, Hugo, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/056,761

(22) Filed: Feb. 29, 2016

(65) Prior Publication Data

US 2016/0177308 A1    Jun. 23, 2016

Related U.S. Application Data

(62) Division of application No. 14/138,690, filed on Dec. 23, 2013, now abandoned.

(60) Provisional application No. 61/746,406, filed on Dec. 27, 2012.

(51) Int. Cl.

| | |
|---|---|
| *A61K 31/70* | (2006.01) |
| *C07H 21/02* | (2006.01) |
| *C07H 21/04* | (2006.01) |
| *C12N 15/115* | (2010.01) |
| *C12N 15/113* | (2010.01) |
| *G01N 33/53* | (2006.01) |
| *C12N 5/00* | (2006.01) |

(52) U.S. Cl.
CPC .......... *C12N 15/115* (2013.01); *C12N 15/113* (2013.01); *G01N 33/5308* (2013.01); *C12N 2310/16* (2013.01); *C12N 2310/18* (2013.01); *C12N 2320/30* (2013.01); *G01N 2500/02* (2013.01)

(58) Field of Classification Search
None
See application file for complete search history.

(56) References Cited

U.S. PATENT DOCUMENTS

2013/0236437 A1    9/2013    Bishopric et al.
2014/0148356 A1    5/2014    Li et al.

OTHER PUBLICATIONS

Ablorh et al., "Accurate quantitation of phospholamban phosphorylation by immunoblot," *Anal. Biochem.*, Jun. 1, 2012; 425(1):68-75.
Antipenko et al., "Interactions of 6-gingerol and ellagic acid with the cardiac sarcoplasmic reticulum $Ca^{2+}$-ATPase," *J. Pharmacol. Exp. Ther.*, Jul. 1, 1999; 290(1):227-234.
Berrebi-Bertrand et al., "Mechanism of action of sarcoplasmic reticulum calcium-uptaek activators—discrimination between sarco(endo)plasmic reticulum $Ca^{2+}$ATPase and phospholamban interaction," *Eur. J. Biochem.*, Aug. 1997; 247:801-809. Available online Jul. 16, 2004.
Buck et al., "Overexpression, purification, and characterization of recombinant Ca-ATPase regulators for high-resolution solution and solid-state NMR studies," *Protein Expr. Purif.*, Aug. 2003; 30(2):253-261.
Cantilina et al., "Comparative studies of cardiac and skeletal sarcoplasmic reticulum ATPases. Effect of a phospholamban antibody on enzyme activation by $Ca^{2+}$," *J. Biol. Chem.*, Aug. 15, 1993; 268(23):17018-17025.
Chiesi et al., "Involvement of electrostatic phenomena in phospholamban-induced stimulation of Ca uptake into cardiac sarcoplasmic reticulum," *FEBS Lett.*, Feb. 1989; 244:241-244.
Chiesi et al., "Reversal of phospholamban-induced inhibition of cardiac sarcoplasmic reticulum $Ca^{(2+)}$-ATPase by tannin," *Biochem. Biophys. Res. Commun.*, Aug. 15, 1994; 202(3):1668-1673.
Davis et al., "Thin filament disinhibition by restrictive cardiomyopathy mutant R193H troponin I induces $Ca^{2+}$-independent mechanical tone and acute myocyte remodeling," *Circ. Res.*, May 25, 2007; 100:1494-1502. Available online Apr. 26, 2007.

(Continued)

*Primary Examiner* — Sean McGarry
(74) *Attorney, Agent, or Firm* — Mueting, Raasch & Gebhardt, PA

(57) ABSTRACT

This disclosure describes, in one aspect, a composition that generally includes an xNA molecule comprising at least six nucleotides, in an amount effective to improve at least one indicator of myocyte function and a pharmaceutically acceptable carrier. In another aspect, this disclosure describes a method of treating cardiac disease. Generally, the method includes administering to a subject a composition that includes an xNA molecule having at least six nucleotides, in an amount effective to improve at least one indicator of myocyte function, and a pharmaceutically acceptable carrier. In another aspect, this disclosure describes a method for evaluating the efficacy of treatment of cardiac disease. Generally, the method includes administering to a subject a composition that includes a first xNA molecule comprising a predetermined length in an amount effective to increase myocyte relaxation, then selecting a predetermined length of a second xNA molecule for at least one subsequent treatment. If treatment with the first xNA results in more myocyte relaxation than is desired, then the predetermined length of the second xNA molecule is shorter than the predetermined length of the first xNA. If, on the other hand, treatment with the first xNA results in less myocyte relaxation than is desired then the predetermined length of the second xNA molecule is longer than the predetermined length of the first xNA.

14 Claims, 20 Drawing Sheets

(56) References Cited

OTHER PUBLICATIONS del Monte et al., "Restoration of contractile function in isolated cardiomyocytes from failing human hearts by gene transfer of SERCA2a," *Circulation*, Dec. 7, 1999; 100(23):2308-2311.

Eizema et al., "Adenovirus-based phospholamban antisense expression as a novel approach to improve cardiac contractile dysfunction: comparison of a constitutive viral versus an edothelin-1-responsive cardiac promoter," *Circulation*, May 9, 2000; 101:2193-2199.

Ha et al., "Controlling the inhibition of the sarcoplasmic $Ca^{2+}$-ATPase by tuning phospholamban structural dynamics," *J. Biol. Chem.*, Dec. 21, 2007; 282(51):37205-37214. Available online Sep. 30, 2007.

Haynes et al., *RNA protein interaction protocols 481*, Humana Press, Totowa, NJ; 1999.

Herron et al., "Calcium-independent negative inotropy by b-myosin heavy chain gene transfer in cardiac myocytes," *Circ. Res.*, Apr. 27, 2007; 100(8):1182-1190. Available online Mar. 15, 2007.

Hughes et al., "Heparin-derived oligosaccharides interact with the phospholamban cytoplasmic domain and stimulate SERCA function," *Biochem. Biophys. Res. Commun.*, Oct. 22, 2010; 401(3):370-375. Available online Sep. 17, 2010.

Karim et al., "Phosphorylation-dependent conformational switch in spin-labeled phospholamban bound to SERCA," *J. Mol. Biol.*, May 12, 2006; 358(4):1032-1040.

Kranias et al., "Modulation of cardiac contractility by the phospholamban/SERCA2a regulatome," *Circ. Res.*, Jun. 8, 2012; 110:1646-1660.

MacLennan et al., "Phospholamban: a crucial regulator of cardiac contractility," *Nat. Rev. Mol. Cell Biol.*, Jul. 2003; 4(7):566-577.

Madden et al., "Cholesterol modulates activity of calcium-dependent ATPase of the sarcoplasmic reticulum," *Nature*, Jun. 7, 1979; 279:538-541.

Mayer et al., "Biochemical and biophysical comparison of native and chemically synthesized phospholamban and a monomeric phospholamban analog," *J. Biol. Chem.*, Jan. 19, 1996; 271(3):1669-1677.

McKenna et al., "Dissociation of phospholamban regulation of cardiac sarcoplasmic reticulum Ca2+ATPase by quercetin," *J. Biol. Chem.*, Oct. 4, 1996; 271(40):24517-24525.

Miyamoto et al., "Adenoviral gene transfer of SERCA2a improves left-ventricular function in aortic-banded rats in transition to heart failure," *PNAS USA*, Jan. 18, 2000; 97(2):793-798.

Murakami et al., "Crystal structure of bacterial multidrug efflux transporter AcrB," *Nature*, Oct. 10, 2002; 419:587-593.

Nimjee et al., "Apatamers: an emerging class of therapeutics," *Annu. Rev. Med.*, Feb. 2005; 56:555-583.

Ogunbayo et al., "Inhibition of the sarcoplasmic/endoplasmic reticulum $Ca^{2+}$-ATPase by flavonoids: a quantitative structure-activity relationship study," *IUBMB Life*, Dec. 2008; 60(12):853-858. Sep. 11, 2008.

Ohizumi et al., "Stimulation of sarcoplasmic reticulum $Ca^{(2+)}$-ATPase by gingerol analogues," *Biol. Pharm. Bull.*, Oct. 1996; 19:1377-1379.

Patil et al., "Plakortides, novel cyclic peroxides from the sponge Plakortis halichondrioides: activators of cardiac SR-$CA^{(2+)}$-pumping ATPase," *J. Nat. Prod.*, Mar. 22, 1996; 59(3):219-223.

Port et al., "Aptamer therapy for heart failure?" *Circle. Res.*, 2011; 109:982-983.

Raghunathan et al., "Structure of the DNA binding domain of *E. coli* SSB bound to ssDNA," *Nat. Struct. Biol.*, Aug. 2000; 7(8):648-652.

Sambrook et al., *Molecular Cloning: A Laboratory Manual, 3rd Edition*, Cold Spring Harbor Press; Cold Spring Harbor, NY, 2001.

Schmidt et al., "Phospholamban: a promising therapeutic target in heart failure?" *Cardiovasc. Drugs Ther.*, Sep. 2001; 15(5):387-396.

Schmidt et al., "Restoration of diastolic function in senescent rat hearts through adenoviral gene transfer of sarcoplasmic reticulum $Ca^{(2+)}$-ATPase," *Circulation*, Feb. 22, 2000; 101:790-796.

Simmerman et al., "Phospholamban: protein structure, mechanism of action, and role in cardiac function," *Physiol. Rev.*, Oct. 1, 1998; 78(4):921-947.

Traaseth et al., "Structure and topology of monomeric phospholamban in lipid membranes determined by a hubrid solution and solid-state NMR approach," *PNAS USA*, Jun. 23, 2009; 106(25):10165-10170. Available online Jun. 9, 2009.

Verardi et al., "Structural topology of phospholamban pentamer in lipid bilayers by a hubrid solution and solid-state NMR method," *PNAS USA*, May 31, 2011; 108:9010-9106. Available online May 16, 2011.

Verma et al., "Modified oligonucleotides: synthesis and strategy for users," *Annu. Rev. Biochem.*, Jun. 1998; 67:99-134.

Wang et al., "Aptamers as therapeutics in cardiovascular diseases," *Curr. Med. Chem.*, Sep. 1, 2011; 18:4169-4174.

Wei et al., "Use of synthetic peptides as tracer antigens in fluorescence polarization immunoassays of high molecular weight analytes," *Anal. Chem.*, Dec. 1993; 65(23):3372-3377.

Xu et al., "Modulation by polyelectrolytes of canine cardiac microsomal calcium uptake and the possible relationship to phospholamban," *J. Biol. Chem.*, Oct. 5, 1989; 264(28):16644-16651.

Soller, "Rheostatic Regulation of the SERCA/Phospholamban Membrane Protein Complex Using Non-Coding RNA and Single-Stranded DNA oligonucleotides," 2015 *Scientific Reports*, 5:13000; 14 pages.

Soller, "Reversal of Phospholamban Inhibition of the Sarco(endo)plasmic Reticulum $Ca^{2+}$-ATPase (SERCA) Using Short, Protein-interacting RNAs and Oligonucleotide Analogs," 2016 *J. Biol. Chemistry*, 291(41):21510-21518.

B

C

THERAPEUTIC POLYNUCLEOTIDES, COMPOSITIONS, AND METHODS

CROSS-REFERENCE TO RELATED APPLICATION

This application is a divisional patent application of U.S. patent application Ser. No. 14/138,690, filed on Dec. 23, 2013, which claims priority to U.S. Provisional Patent Application No. 61/746,406, filed Dec. 27, 2012, each of which is incorporated herein by reference.

GOVERNMENT FUNDING

This invention was made with government support under GM063533, GM064742, and GM072701 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "110-03900101_SequenceListing_ST25.txt" having a size of 4 kilobytes and created on Dec. 20, 2013. The information contained in the Sequence Listing is incorporated by reference herein.

SUMMARY

This disclosure describes, in one aspect, a composition that generally includes an xNA molecule comprising at least six nucleotides, in an amount effective to improve at least one indicator of myocyte function and a pharmaceutically acceptable carrier.

In some embodiments, the xNA molecule may be a ssDNA molecule of no more than 100 nucleotides. In other embodiments, the xNA molecule may be an RNA of no more than 50 nucleotides.

In some embodiments, the xNA molecule can include a randomized nucleotide sequence.

In some embodiments, the xNA molecule may be contained in vector.

In some embodiments, the indicator of myocyte function can include relaxation and the improvement of myocyte relaxation can include reducing the time required to return to baseline after contraction.

In another aspect, this disclosure describes a method of treating cardiac disease. Generally, the method includes administering to a subject a composition that includes an xNA molecule having at least six nucleotides, in an amount effective to improve at least one indicator of myocyte function, and a pharmaceutically acceptable carrier.

In another aspect, this disclosure describes a method for evaluating the efficacy of treatment of cardiac disease. Generally, the method includes administering to a subject a composition that includes a first xNA molecule comprising a predetermined length in an amount effective to increase myocyte relaxation, then selecting a predetermined length of a second xNA molecule for at least one subsequent treatment. If treatment with the first xNA results in more myocyte relaxation than is desired, then the predetermined length of the second xNA molecule is shorter than the predetermined length of the first xNA. If, on the other hand, treatment with the first xNA results in less myocyte relaxation than is desired then the predetermined length of the second xNA molecule is longer than the predetermined length of the first xNA.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
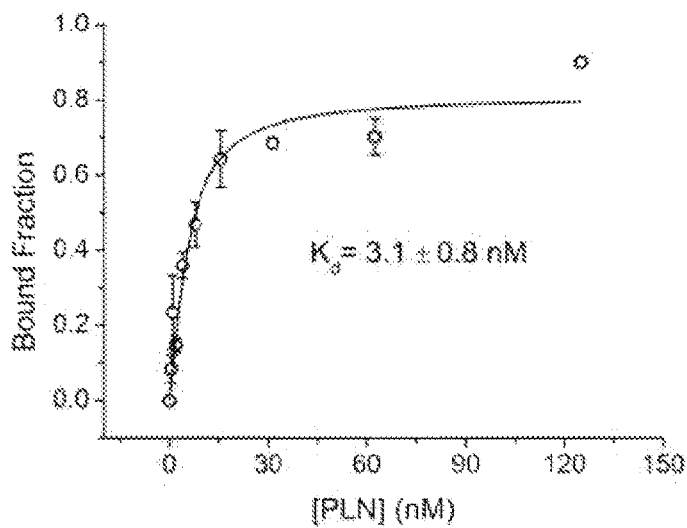
FIG. 1. Binding curves demonstrating affinity of random sequence ssDNA (80 mer, FAM labeled) measured using (A) fluorescence polarization, (B) affinity capillary electrophoresis and (C) native gel mobility shift assays.
Figure 1:
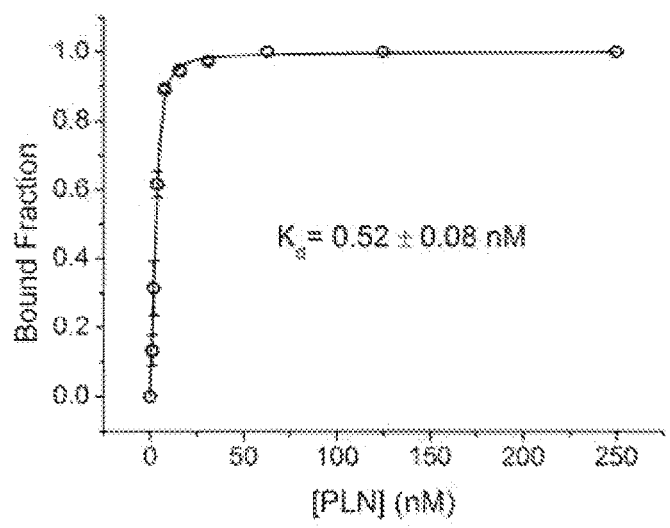
Figure 1:
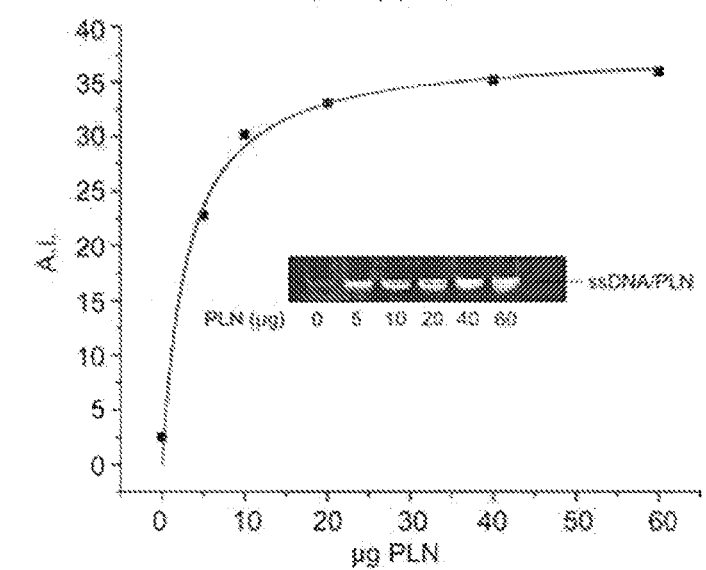

This disclosure describes therapeutic polynucleotides, compositions that include therapeutic polynucleotides, and methods that involve the therapeutic polynucleotides. Generally, we disclose that single-stranded polynucleotides modulate PLN-mediated inhibition of SERCA in a tunable manner that is, surprisingly, independent of the nucleotide sequence of the polynucleotide. Rather, the tunability of the system correlates with the length of the polynucleotide.

As used herein, the following terms and abbreviations shall have the indicated meanings:

"xNA" generically refers to a single-stranded polymer of nucleotides and/or nucleotide analogs. The term "xNA" therefore includes, for example, ssDNA (in either the D or L conformation), RNA, 2'-O-methyl DNA, 2'-fluoro-DNA, and mixtures thereof.

"PLN" refers to phospholamban.

"SR" refers to sarco(endo)plasmic reticulum.

"SERCA" refers to sarco(endo)plasmic reticulum $Ca^{2+}$-ATPase.

"DPC" refers to dodecylphosphocholine.

"DOPC" refers to 1,2-dioleoyl-sn-glycero-3-phosphocholine.

"DOPE" refers to 1,2-dioleoyl-sn-glycero-3-phosphoethanolamine.

"Randomized nucleotide sequence" refers to a polynucleotide sequence selected or designed without regard to any sequence-specific binding to another molecule. Thus, a "randomized nucleotide sequence" need not be synthesized randomly. In this regard, a "randomized nucleotide sequence" may be designed with any degree of particularity for other functional properties such as, for example, nuclease protection, secondary structure, ease of synthesis, etc.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Heart muscle contractility is signaled by $Ca^{2+}$ ions that enter the sarcolemma membrane in response to an action potential. A small influx of $Ca^{2+}$ stimulates the larger release of $Ca^{2+}$ ions from the sarcoplasmic reticulum storage via the ryanodine receptors. In the cytoplasm $Ca^{2+}$ binds the troponin complex initiating contraction (systole). Relaxation (diastole) is orchestrated by a membrane protein complex between the sarcoplasmic reticulum $Ca^{2+}$-ATPase (SERCA) and phospholamban (PLN). Powered by ATP, SERCA transports two ions of $Ca^{2+}$ per enzymatic turnover in exchange for three $H_3O^+$ ions. Unphosphorylated PLN binds SERCA within the membrane and reduces its apparent $Ca^{2+}$ affinity. Following β-adrenergic stimulation, PLN is phosphorylated at Ser-16, reversing the inhibitory action, reestablishing $Ca^{2+}$ flux (MacLennan et al., *Nat. Rev. Mol. Cell Biol.* 4:566-577 (2003)). Proper control of $Ca^{2+}$ concentration throughout the pumping cycle is necessary for maintaining a healthy heart.

There is a direct link between dysregulation of $Ca^{2+}$ cycling in muscle cells and development of heart failure. Impaired SR function—i.e., mishandling of $Ca^{2+}$ during diastole and systole—is a common defect in cardiomyocytes from failing hearts (Schmidt et al., *Cardiovasc. Drugs Ther.* 15:387-396 (2001)). For this reason, stimulation of SERCA's activity is one strategy for treating heart disease. One way to improve SR $Ca^{2+}$ uptake is by disrupting the SERCA/PLN inhibitory complex. In particular, enhanced SERCA activation can be attained using monoclonal antibodies against the N-terminus of PLN (Cantilina et al., *J. Biol. Chem.* 268:17018-17025 (1993); Mayer et al., *J. Biol. Chem.* 271:1669-1677 (1996)), charged detergents (Mayer et al., *J. Biol. Chem.* 271:1669-1677 (1996; Chiesi et al., *FEBS Lett.* 244:241-244 (1989)), tannin (Chiesi et al., *Biochem. Biophys. Res. Commun.* 202:1668-1673 (1994)) and heparin derived compounds (Xu et al., *J. Biol. Chem.* 264:16644-16651 (1989); Hughes et al., *Biochem. Biophys. Res. Commun.* 401:370-375 (2010)). However, the mechanism of action for such molecules and their effect on the contractile parameters in live cardiac cells has not been determined.

A further complication for SERCA-inducing drug design stems from the intrinsic role of PLN within the regulatory complex. PLN does not act as a simple on/off switch for SERCA; rather it modulates SERCA's function via a conformational equilibrium between a T state (the inhibitory ground state) and an R state (the non-inhibitory excited state), which is shifted upon PLN phosphorylation at Ser-16. In the ground state PLN is L-shaped, with the transmembrane (TM) domain crossing the SR membrane and the N-terminal cytoplasmic domain embedded onto the membrane surface (Verardi et al., *Proc. Natl. Acad. Sci. U.S.A* 108:9101-9106 (2011); Traaseth et al., *Proc. Natl. Acad. Sci. U.S.A* 106:10165-10170 (2009)). The transmembrane domains in both the T and R states bind SERCA. Only the cytoplasmic domain of the R state, however, interacts with the enzyme headpiece. Shifting the equilibrium toward the T state augments SERCA inhibition, while promoting the R state relieves the inhibition. A proper balance between the two states promotes the correct regulation of SERCA within a physiological window of inhibition. PLN regulation outside this window (super-inhibition or total loss of inhibitory function) can promote the progression of heart pathologies such as, for example, dilated cardiomyopathies.

Therefore, an ideal drug for SERCA activation should have the following features: 1) a predictable and tunable effect on SERCA's activity, 2) a straightforward mechanism for delivery to the affected tissues, 3) stability over long periods in the context of the cell, and 4) be easy to produce in large quantities and at reasonable costs. We demonstrate herein that single-stranded xNAs oligonucleotides such as, for example, ssDNA, RNA, or 2'-O-methyl DNA may serve as a platform for developing such drugs. xNAs can bind PLN in the nM range, effectively releasing its inhibitory effect on SERCA activity. Our activity and binding assays show that xNA inhibition of PLN is length-dependent, allowing SERCA to be tuned across an effective activity range. Surprisingly, no sequence dependence was observed. Solid-state NMR and fluorescence spectroscopy reveal that ssDNA, an exemplary xNA, binds the cytoplasmic domain Ia of PLN, targeting arginines and aromatic residues. Thus, our results allow the design and development of a new class of compounds designed to selectively bind to PLN and tune SERCA inhibition and $Ca^{2+}$ transport. We further describe methods of tunably modulating SERCA inhibition and $Ca^{2+}$ transport.

First, we assessed the affinities of a group of ssDNA sequences for PLN. Table 1 lists the ssDNA sequences tested.

TABLE 1

Random ssDNA sequences used.

| Sequence Length | Sequence 5'→3' | SEQ ID NO: |
|---|---|---|
| 5 | FAM-GCTTG | 1 |
| 10 | FAM-ATAGCTTGCA | 2 |
| 15 | FAM-AGTGATAGCT ATGGT | 3 |
| 20 | FAM-AGCAGCACAG AGGTCAGATG | 4 |
| 30 | FAM-ACTGAGCATG GGATAACCGT TCTCAGACTT | 5 |
| 50 | FAM-AGCAGCACAG AGGTCAGATG CAGGTAGGGT CCTATGCGTG CTACCGTGAA | 6 |
| 80* | FAM-(N)$_{80}$ | 7 |

*A mixture of randomized 80-mer ssDNA sequences ssDNA were chosen to determine the effect of both length and sequence on affinity. Most of the sequences assessed do not possess any significant secondary structure. The 30-mer is an exception that is predicted to exhibit internal hybridization and was included to determine the effect of secondary structure on affinity for PLN. The 80-mer was synthesized as a random mixture with an equal probability of possessing each base at every register position. This ssDNA was chosen to assess affinity independently of a specific sequence. Any measure made using the 80-mer should therefore be interpreted as an average sampling across the entire population of possible ssDNA sequences.

Three independent techniques were used to determine ssDNA affinities for PLN: affinity capillary electrophoresis (ACE), fluorescence polarization (FP), and a native gel mobility shift assay. In these experiments, a series of solutions were prepared by adding ssDNA to solutions of increasing PLN concentration (dissolved in 0.1% $C_{12}E_8$ detergent). FIG. 1 shows examples of binding curves recorded using ACE and FP. Both curves demonstrate strong affinity between the 80-mer ssDNA and PLN with low nM dissociation constants (KO. Similarly, the native gel mobility shift assay clearly demonstrated formation of a ssDNA-PLN complex.

Table 2 shows the dissociation constants measured for some of the ssDNA sequences listed in Table 1. Sequence length was determined to be the primary predictor of affinity for PLN with ssDNA sequences shorter than 10 bases demonstrating significantly higher dissociation constants. Longer sequences all exhibited low nM dissociation constants for PLN. Surprisingly, this high affinity for PLN was independent of ssDNA sequence. This is reinforced by the high affinity demonstrated by the pool of random sequence 80-mer ssDNA. A notable exception is the 30-mer, which demonstrated slightly weaker affinity for PLN than the other sequences tested. As stated above, the 30-mer chosen here has significant internal secondary structure. The energetically unfavorable unfolding process required to linearize the 30-mer may contributes to its weaker affinity for PLN.

TABLE 2

Dissociation Constants ($K_d$) of the ssDNA-PLN complexes.

| Sequence Length (SEQ ID NO:) | $K_d$ (nM) FP | ACE |
|---|---|---|
| 10 (SEQ ID NO: 2) | 35 ± 5 | 260 ± 180 |
| 15 (SEQ ID NO: 3) | 3.1 ± 0.5 | 80 ± 40 |
| 20 (SEQ ID NO: 4) | 1.8 ± 0.6 | 6.5 ± 0.9 |
| 30 (SEQ ID NO: 5) | 21 ± 1 | 24 ± 5 |
| 50 (SEQ ID NO: 6) | 5 ± 1 | 1.2 ± 0.4 |
| 80* (SEQ ID NO: 7) | 3.1 ± 0.8 | 0.5 ± 0.1 |

*Confidence intervals are the standard deviation (n = 3).

Double stranded DNA was also tested and did not demonstrate measurable affinity for PLN.

Figure 3:
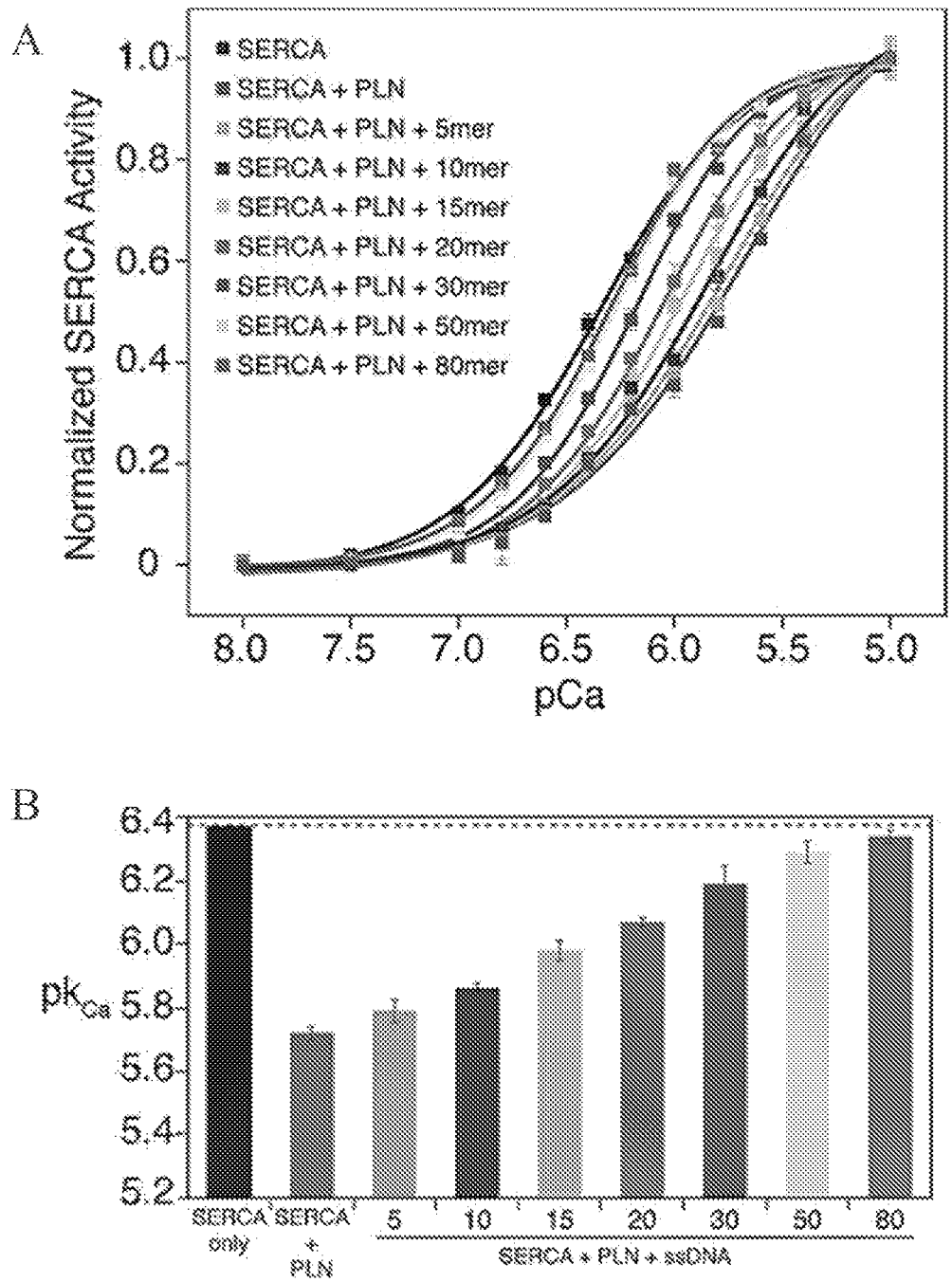
FIG. 3. $Ca^{2+}$-ATPase activity assay in DOPC/DOPE vesicles. A) Normalized SERCA activity as function of $Ca^{2+}$ concentration in the presence of ssDNA of different length. B) summary of pCa values at half maximum activity of SERCA (calculated from A) with and without PLN and ssDNA.

Next, we performed coupled enzyme assays to determine the effect of ssDNA on SERCA function. In these assays SERCA and PLN were reconstituted in DOPC/DOPE lipid vesicles and the apparent $Ca^{2+}$ affinity of SERCA was measured in the presence and absence of pentameric PLN. FIG. 3A is a plot of normalized SERCA activity at varying concentrations of free calcium (pCa). The $pK_{Ca}$ is defined as the value of pCa at half maximum activity, which corresponds to the apparent calcium affinity of SERCA. PLN inhibits SERCA by decreasing the $pK_{Ca}$ as evidenced by the curve depicting SERCA+PLN shifting to the far right in FIG. 3A. Adding ssDNA reverses the effect, relieving the inhibitory effect of PLN. FIG. 3 demonstrates that ssDNA sequence length determines the extent to which PLN inhibition is reversed. Shorter oligonucleotide sequences shift the $pK_{Ca}$ only modestly. In contrast, ssDNA sequences longer than 80 nucleotides can achieve complete reversal of PLN inhibition. The complete reversal of PLN inhibition compares well with reported effects of PLN phosphorylation at Ser-16 by protein kinase A (Karim et al., *J. Mol. Biol.* 358:1032-1040 (2006); Simmerman et al., *Physiol. Rev.* 78:921-947 (1998)).

Figure 2:
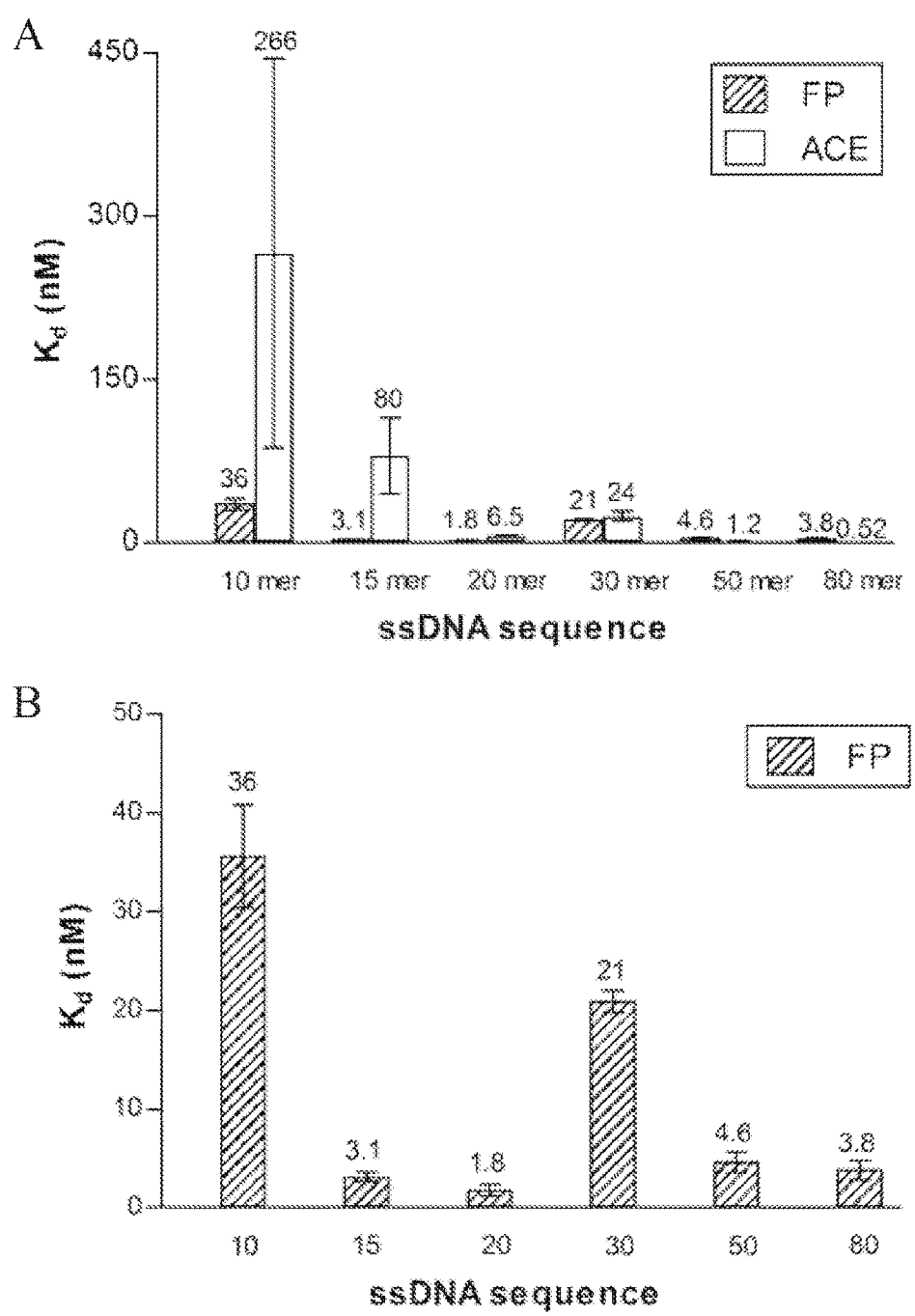
FIG. 2. Binding affinity of ssDNA to PLN measured by fluorescence polarization (FP) and affinity capillary electrophoresis (ACE). A) Comparison of FP and ACE. The latter gives substantially higher values and larger errors for short ssDNA sequences. B) Same as A, but without the data from ACE.
Figure 12:
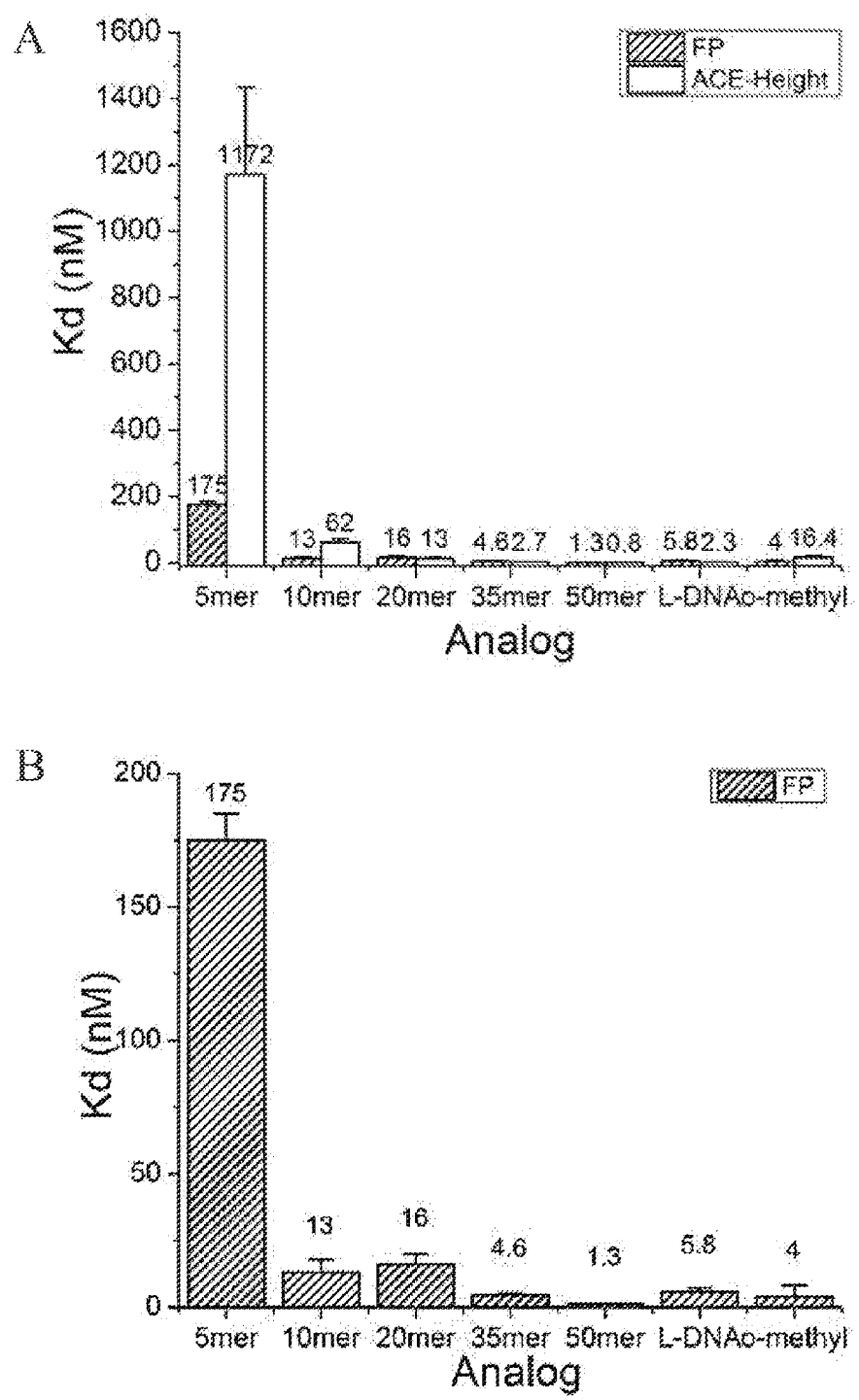
FIG. 12. Binding affinity of various xNAs to PLN measured by fluorescence polarization (FP) and affinity capillary electrophoresis (ACE). A) Comparison of FP and ACE. The latter gives substantially higher values and larger errors for the RNA 5-mer sequences. B) Same as A, but without the data from ACE.
Figure 13:
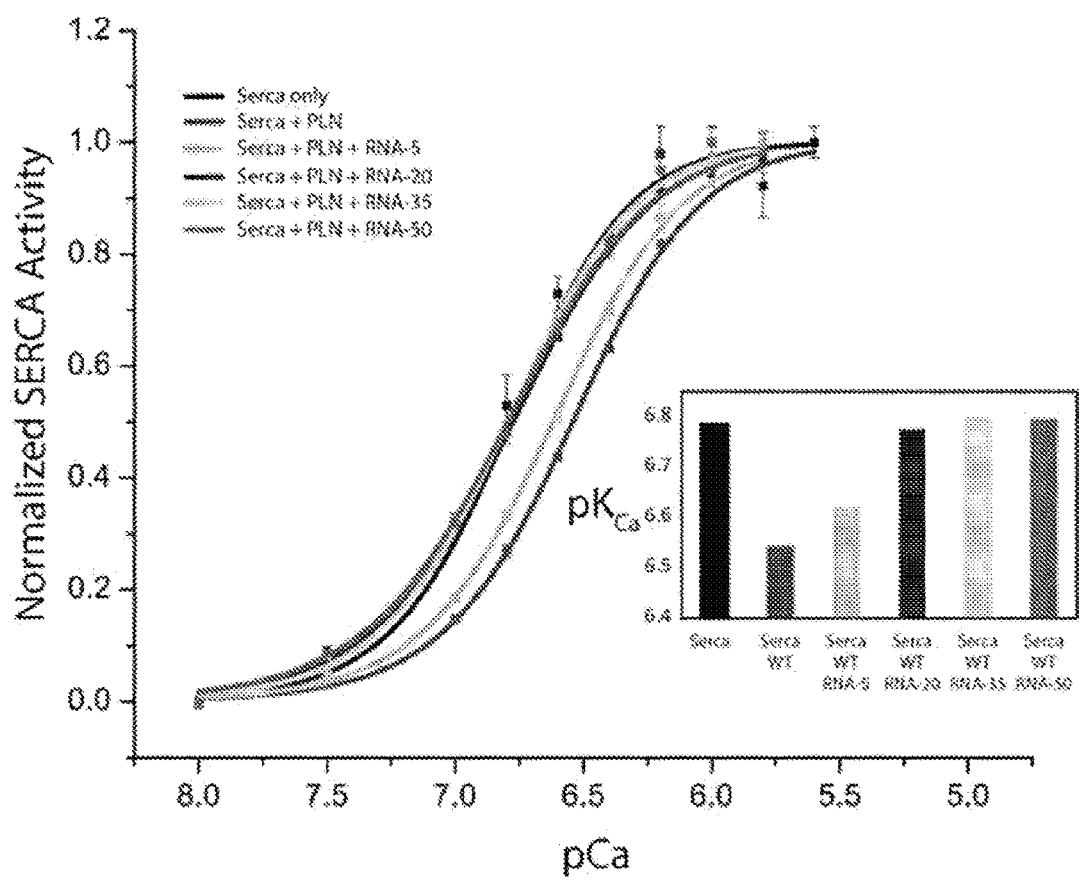
FIG. 13. $Ca^{2+}$-ATPase activity assay in DOPC/DOPE vesicles. A) Normalized SERCA activity as a function of $Ca^{2+}$ concentration in the presence of RNAs of different lengths.

RNA produced a result similar to that observed using ssDNA. Random sequences of RNA had affinities for PLN that were similar to or greater than affinity between PLN and a ssDNA of similar length. (e.g., compare ssDNA $K_d$ shown in FIG. 2 with RNA $K_d$ shown in FIG. 12). As with ssDNA, RNA binding affinity decreased for RNA sequences as short as 5 bases. The RNAs also reversed PLN inhibition of SERCA activity in a length-dependent manner, as shown in FIG. 13. FIG. 13 also demonstrates that RNA is somewhat more potent than ssDNA at rescuing PLN inhibition of SERCA activity. As noted above, ssDNA sequences longer than 80 nucleotides achieve complete reversal of PLN inhibition. (FIG. 3B). RNA sequences, however, achieve complete reversal of PLN inhibition at a length of 20 nucleotides. (FIG. 13, inset).

Figure 4:
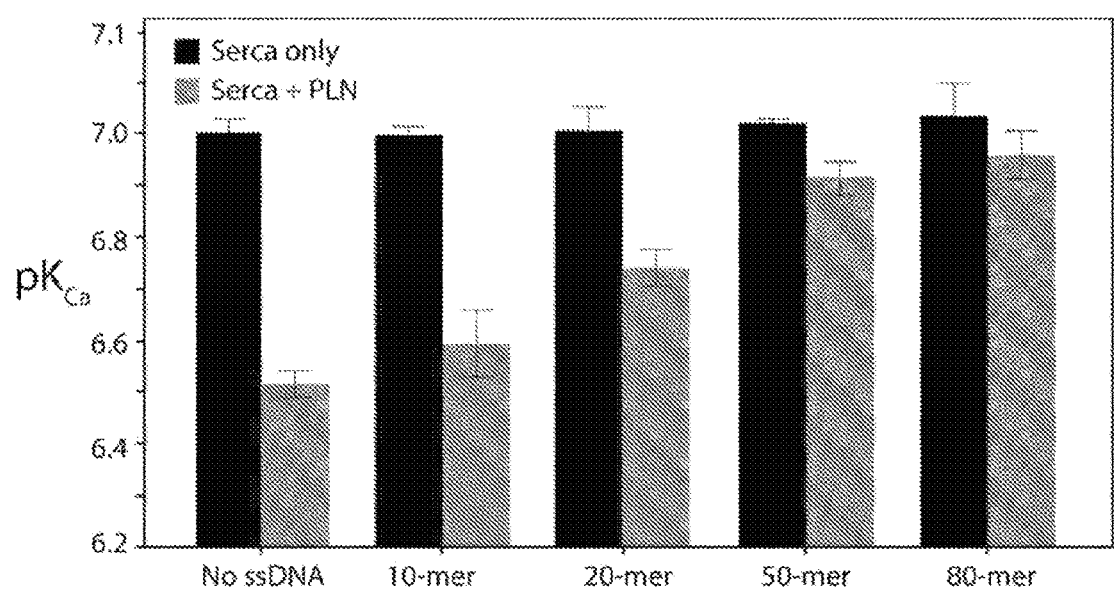
FIG. 4. Single-stranded DNA interferes with the SERCA/PLN complex and not with SERCA alone.

FIG. 4 demonstrates that ssDNA has no direct effect on the $pK_{Ca}$ of SERCA in the absence of PLN (black), reinforcing the premise that xNAs interact with PLN, not SERCA.

Figure 5:
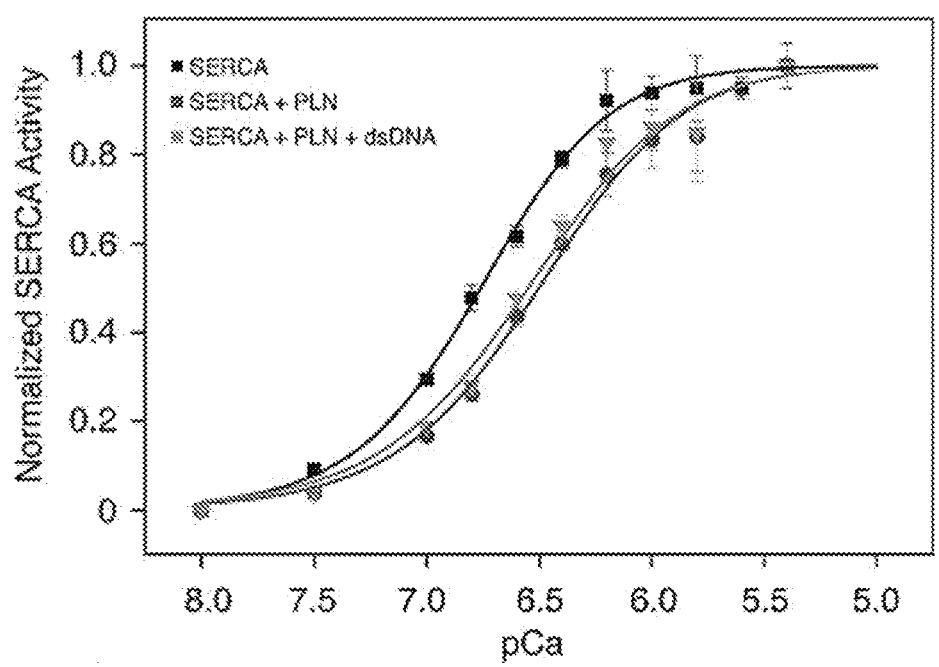
FIG. 5. Effect of double-stranded DNA (A) and free dNTPs (B) on SERCA inhibition.
Figure 5:
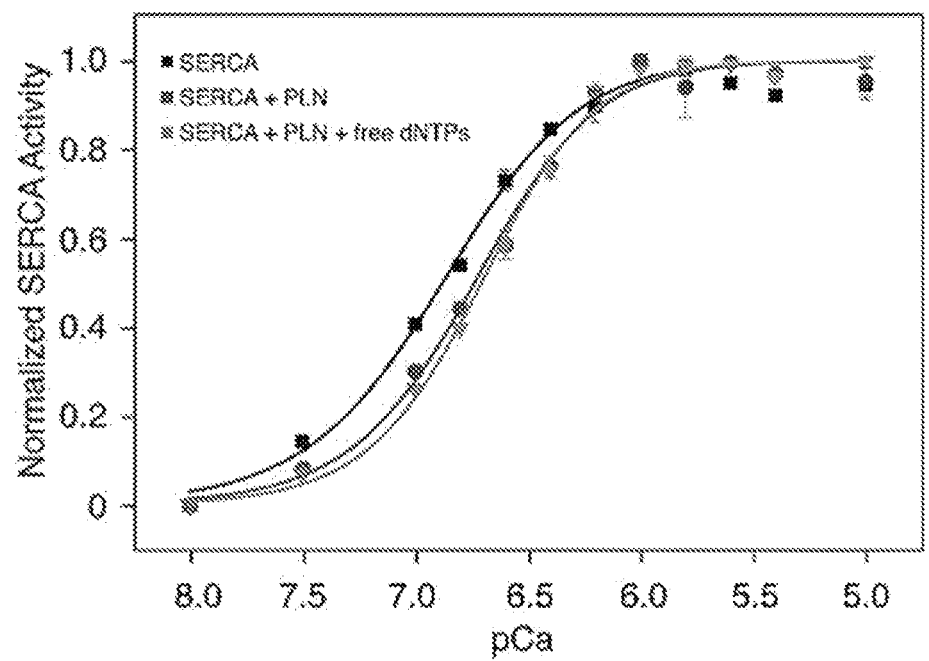

FIG. 5 shows the coupled enzyme assays carried out with double-stranded DNA and a mixture of free deoxynucleotide triphosphates (dNTPs). Double-stranded DNA does not interact with PLN and does not relieve SERCA inhibition. Also, addition of free deoxynucleotide triphosphates (dNTPs) at the same effective concentrations of ssDNA has no effect on SERCA activity.

Figure 6:
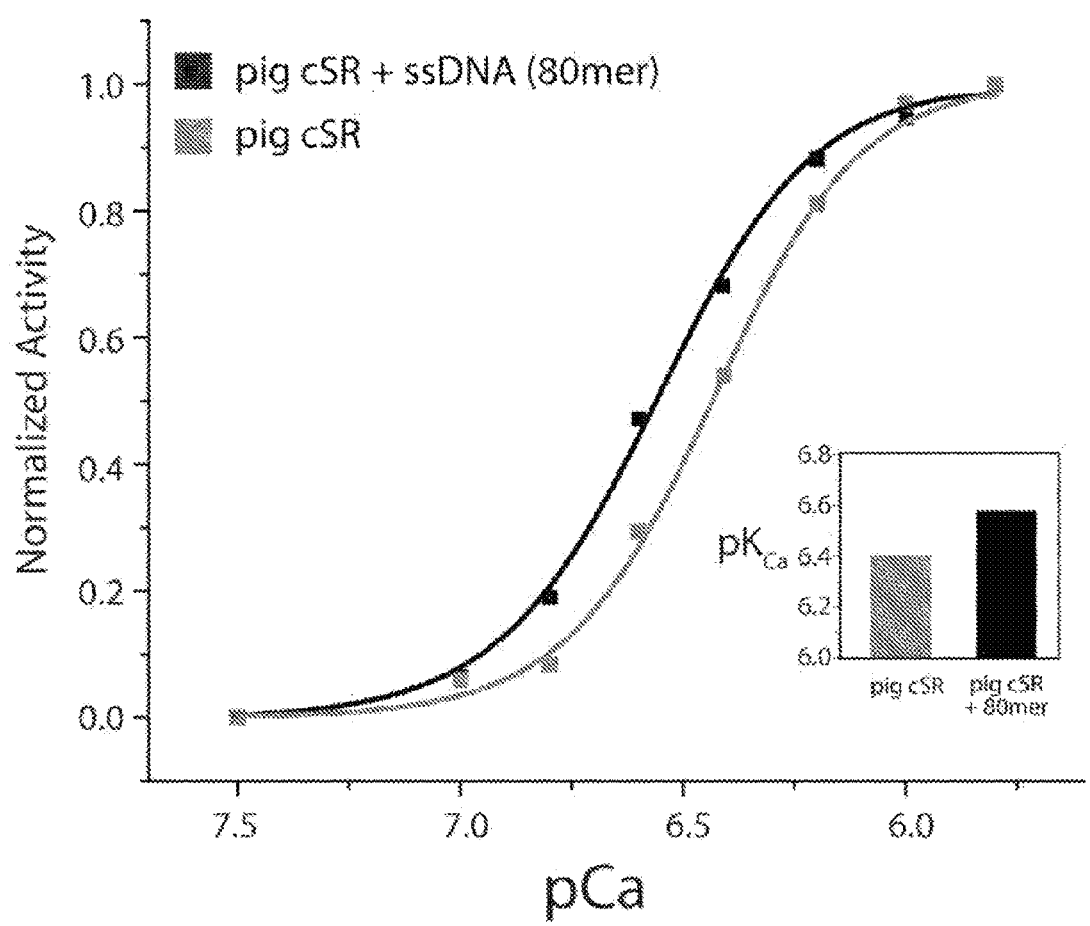
FIG. 6. Effect of ssDNA on pig cardiac SR. Pig cSR vesicles (20 μg total protein) were assayed for SERCA activity using the coupled enzyme assay in the presence (black curve) and absence (grey curve) of 1 μM ssDNA (80-mer).

We repeated the coupled enzyme assay using cardiac SR vesicles extracted from pig ventricles (pig cSR), which endogenously express PLN, to verify that the observed inhibitory effect of xNAs on PLN is also observed in the cardiac SERCA isoform (SERCA2a). FIG. 6 shows that incubating pig cSR vesicles with 1 μM ssDNA (80-mer) increased the $pK_{Ca}$ by 0.15, confirming the efficacy of xNAs on the native SERCA2a/PLN complex.

Figure 7:
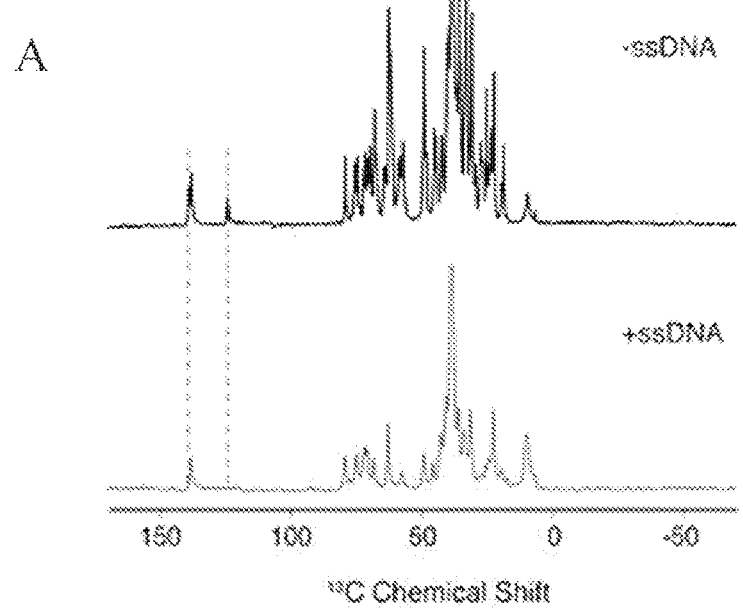
FIG. 7. Mapping of PLN residues involved in ssDNA binding. A) Overlay of two refocused-INEPT experiments correlating $^1H$ chemical shift to $^{13}C$ chemical shift of PLN in DMPC lipid vesicles in the presence (grey) and absence (black) of ssDNA. Asterisks indicate lipid signals. Inset: Arginine Cζ side chain peaks. B) Expanded region from panel A (dotted area) showing tentative assignment of Cα atoms shifting upon addition of ssDNA (grey spectrum).
Figure 7:
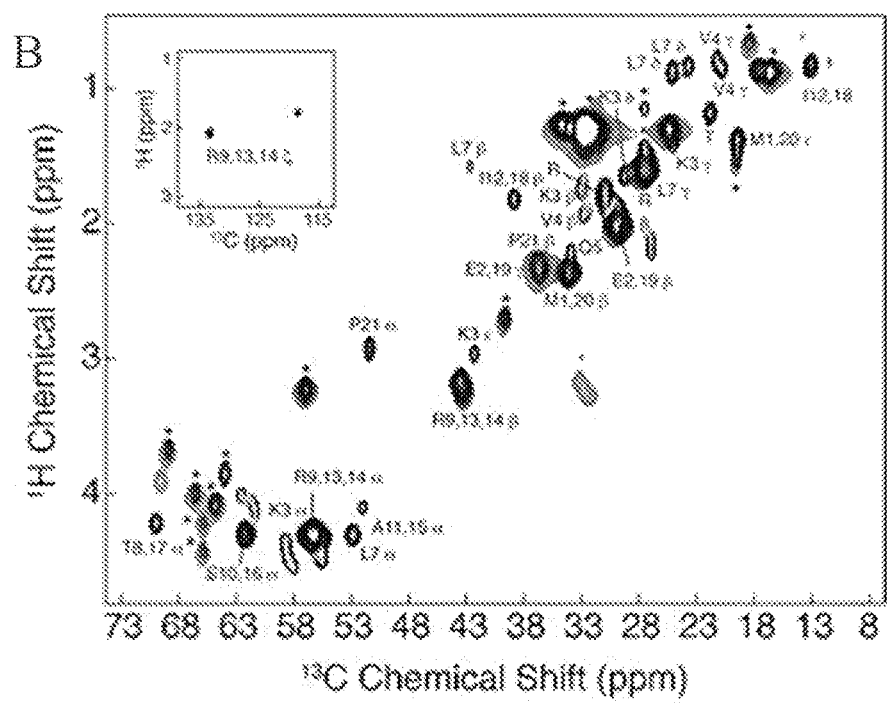

To identify the residues of PLN that interact with xNAs, we reconstituted PLN in lipid vesicles and used $^{13}$C-edited MAS ssNMR experiments to probe the resonances corresponding to the backbone and side chains. A lipid composition that closely mimics the SR membrane was chosen for these experiments. To probe the resonances of the dynamic cytoplasmic helix of PLN, we used a refocused INEPT (rINEPT) experiment that filters out the resonances corresponding to the more rigid residues of the TM domain. FIG. 7 shows the spectra for PLN in the absence (black) and presence (grey) of ssDNA (80 nucleotides) at 1:1 molar ratio. The addition of ssDNA to PLN causes an overall attenuation and broadening of the signals (FIG. 7A) due to the increase in rotational correlation time of the cytoplasmic α-helix upon ssDNA binding. The same effect is apparent in the resonances present in the 2D [$^1$H-$^{13}$C]-rINEPT spectra, where most resonances dramatically broaden out, with several cases resonances broaden out beyond detection. In contrast, the resonances associated with the lipids remain unperturbed (FIG. 7B). By analyzing the spectra before and after addition of ssDNA, it appears that residues in PLN involved in the binding are three arginines (Arg-9, Arg-13, and Arg-14), the lysine at position 3 (Lys-3) and the Glutamate at position 19 (Glu-19).

Figure 14:
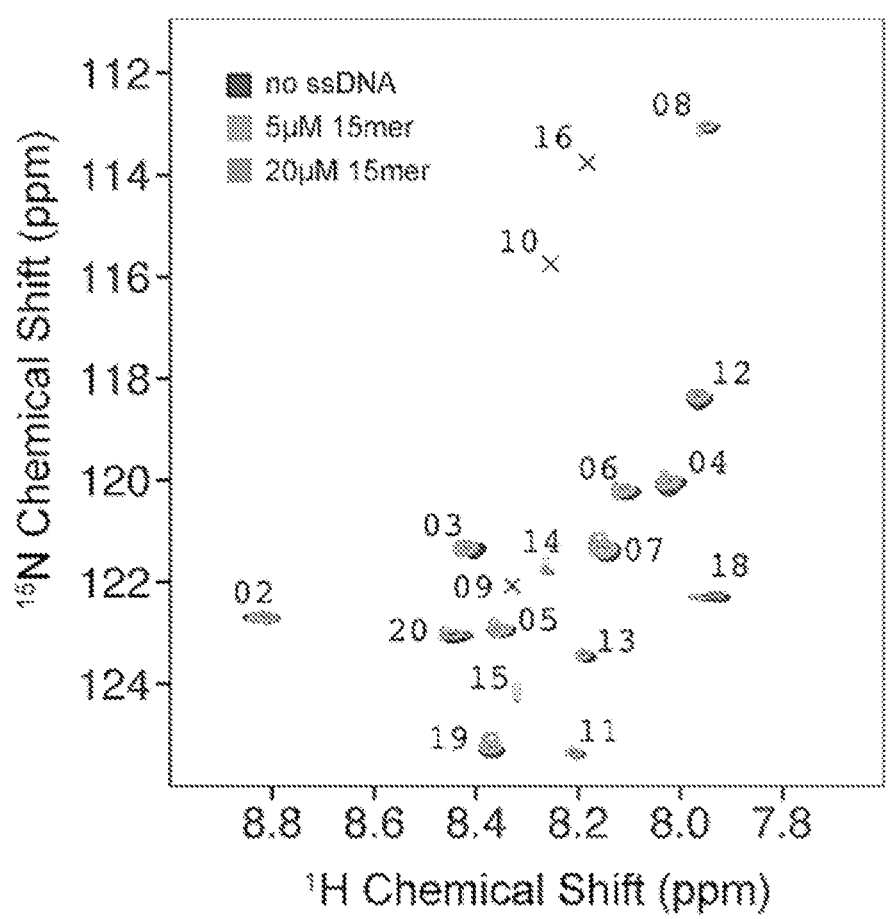
FIG. 14. Titration of PLN in isotropic bicelles with 15-mer ssDNA. Overlay of $^{15}N$ HSQC spectra recorded after addition of increasing concentration of 15-mer ssDNA. Only the most mobile residues (2-20) are visible in the spectrum due to increase in rotational correlation time of the bicelles/protein complex.

Similar results are also obtained by solution NMR investigation of PLN dissolved in isotropic bicelles (q=0.33). FIG. 14 shows the overlay of three $^{15}$N-HSQC spectra obtained after titration with increasing concentration of 15-mer ssDNA. Several resonances in the cytoplasmic domain (Lys-3, Arg-14, Glu-19, and Met-20) appear to be affected by the binding of 15-mer ssDNA.

Mishandling of $Ca^{2+}$ by the sarcoplasmic reticulum is a common characteristic of many cardiomyopathies. Various cardiomyopathies can have different etiologies such as, for example, pathologically low SERCA/PLN ratios, hindered or lack of PLN phosphorylation, and/or single-site genetic mutations in PLN sequence or promoter (Kranias et al., *Circ. Res.* 110:1646-1660 (2012)). Each of these pathologies can lead to reduced muscle contractility and progression of heart disease.

Several possible strategies for treating these cardiomyopathies have been proposed and investigated. These strategies include, for example, SERCA overexpression via adenovirus gene transfer, PLN knockout (via siRNA techniques), SERCA activation via drugs, and gene therapy using PLN loss-of-function (i.e., dominant-negative) mutants (Ohizumi et al., *Biol. Pharm. Bull.* 19:1377-1379 (1996; Antipenko et al., *J. Pharmacol. Exp. Ther.* 290:227-234 (1999); Patil et al., *J. Nat. Prod.* 59:219-223 (1996); Berrebi-Bertrand et al., *Eur. J. Biochem.* 247:801-809 (1997); Miyamoto et al., *Proc. Natl. Acad. Sci. U.S.A* 97:793-798 (2000); Schmidt et al., *Circulation* 101:790-796 (2000); del Monte et al., *Circulation* 100:2308-2311 (1999)). Ablation of PLN in higher mammals (e.g., rabbits and humans) can lead to heart failure, however, while adenovirus gene transfer of PLN dominant-negative is still a nascent technology (Eizema et al., *Circulation* 101:2193-2199 (2000)), and SERCA overexpression is now in phase III of clinical trials (Kranias et al., *Circ. Res.* 110:1646-1660 (2012)). Nonetheless, the manifestations of cardiomyopathies can be quite diverse and no there currently is no universally effective therapy for all of the different phenotypes and genotypes has been identified. Therefore, pharmacological approaches involving small molecules that interfere with the SERCA/PLN complex and augment muscle contractility remain a promising therapeutic option.

Various research groups have demonstrated that charged detergents, heparin-derived compounds, the polyphenol tannin, and/or a plant-derived flavonoid such as quercetin can reverse SERCA inhibition by PLN. (Mayer et al., *J. Biol. Chem.* 271:1669-1677 (1996); Chiesi et al., *FEBS Lett.* 244:241-244 (1989); Chiesi et al., *Biochem. Biophys. Res. Commun.* 202:1668-1673 (1994); Xu et al., *J. Biol. Chem.* 264:16644-16651 (1989); Hughes et al., *Biochem. Biophys. Res. Commun.* 401:370-375 (2010); Ogunbayo et al., *IUBMB Life* 60:853-858 (2008)). Whereas tannin, charged detergents, and heparin disrupt the SERCA/PLN complex by binding to N-terminus of PLN, quercetin specifically binds SERCA, competing with the PLN binding groove (McKenna et al., *J. Biol. Chem.* 271:24517-24525 (1996)). These compounds, however, exhibit relatively weak affinity for PLN with dissociation constants in the high micromolar range, e.g., having a $K_d$>100 µM. In addition, the effects of these molecules on the SERCA/PLN complex cannot be easily tuned, making it challenging to determine an effective dosing range.

In contrast, our approach involves using xNA to reverse SERCA inhibition by PLN. xNAs have a high affinity for PLN: each of ssDNA and RNA exhibits dissociation constants in the range of 1 nM to 20 nM. FIG. 4 shows that ssDNA does not have any discernible direct effect on SERCA (FIG. 4, black histograms). FIG. 5 shows that neither double-stranded DNA nor a mixture of free dNTP reverses PLN function (FIG. 5B).

Moreover, the extent of SERCA activation can be tuned using xNA. ssDNA sequences shorter than 20 nucleotides had relatively higher dissociation constants for PLN and a relatively modest effect restoring SERCA activity. Longer ssDNA nucleotide sequences exhibit lower dissociation constants for PLN and more completely reverse PLN inhibition of SERCA. Similar results are observed using RNA as the xNA, though the RNA sequences appear to have more potency, meaning that full restoration of SERCA activity can be achieved using a shorter sequence than, for example, ssDNA. Moreover, the effectiveness of reversing PLN inhibition of SERCA is determined by xNA length and is independent of the particular nucleotide sequence of the xNA. Indeed, full SERCA activation (i.e., complete reversal of PLN inhibition) generated effects similar those observed via phosphorylation of PLN at Ser-16. Consequently, the therapeutic use of xNA offers the ability to tune therapy.

This tunability may be structurally related to the PLN binding site rather than merely a reflection of the relative affinities of the xNAs for PLN. The concentrations of ssDNA used to generate the data shown in FIG. 1 were well above the dissociation constants listed in Table 2, suggesting that PLN was fully saturated with ssDNA in these experiments. A certain length of xNA is required to fully inhibit PLN, but that length may vary between different species of xNA. The 30-mer ssDNA further supports this concept since it fits the activity trend shown in FIG. 3 even though its secondary structure gives rise to a higher dissociation constant for PLN than unstructured sequences of similar length (see Table 2). This ability to tune the effectiveness of PLN inhibition by a mechanism other than ligand concentration suggests a powerful approach for dosing to a desired effect, an important consideration when regulating heart function to a desired range.

In recent years, short ssDNA or RNA molecules that selectively bind to protein targets with high affinity have been used to treat several conditions. These ssDNA or RNA molecules can act similar to antibodies. For PLN, specific antibodies target the cytoplasmic domain detaching it from the complex. The xNAs may act on PLN with a similar mechanism. However, unlike the antibodies, xNAs offer advantages over antibodies such as, for example, having greater stability in different cellular environments and/or being easily modified by chemical methods for nuclease stability[35]. In our case, we found that the effect of the xNA molecules is tunable, which implies a higher level of control for their biological function. Moreover, we discovered that the xNAs vary somewhat in potency, lending a further expansion of tunability. For example, if a more potent effect is desired, RNA may be used as the xNA. RNA exhibits full reversal of PLN-mediated SERCA inhibition using with RNAs of about 20 nucleotides. If, however, one desires greater tunability precision, then ssDNA can be used. Full reversal of PLN-mediated SERCA inhibition is observed using ssDNA of about 80 nucleotides, with a more gradual increase in a length-correlated effect than is observed with RNA.

We next investigated the effects of ssDNA on the contractility of myocytes. Generally, rat myocytes were transfected with ssDNA, then assessed for function by evaluating sarcomere length dynamics and/or calcium transient dynamics. Baseline sarcomere length is the starting length between sarcomeres and is a measure of the diastolic tone of cardiac myocytes. Peak amplitude is the maximum amplitude of sarcomere shortening, a measure of contractility of a cardiac myocyte and relating to systolic performance of the heart. Fractional shortening is the percent of the peak amplitude in comparison to the baseline sarcomere length and is another measure of the systolic performance of a cardiac myocyte. Peak time is a measure of the time it takes from the start of a contraction to the maximum sarcomere shortening. Time to baseline (BL) 25-75% are the time it takes a myocyte to return from the peak amplitude to 25-75% of the baseline sarcomere length. These are measures of the relaxation of the cardiac myocyte and are indicative of diastolic performance in the heart. Baseline Calcium is the relative level of diastolic calcium in the cytoplasm. Peak amplitude is the maximum amount of calcium in the cytosol during a calcium transient. The time measures are the same as for sarcomere length only monitoring the calcium transient.

Figure 8:
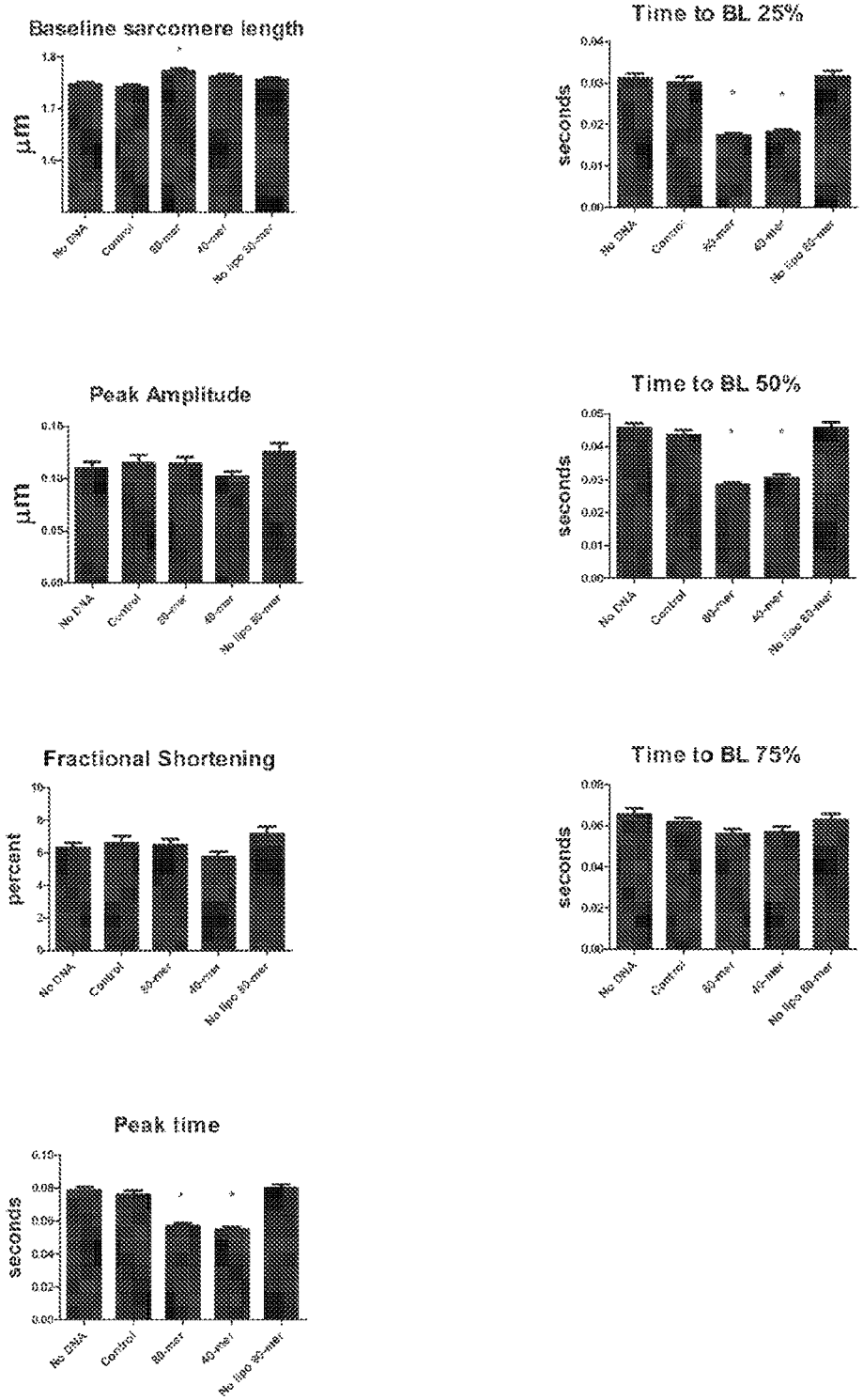
FIG. 8. Sarcomere length dynamics reveal ssDNA increases relaxation. ssDNA 80-mer and 40-mer have no effect on the contractility measures of peak amplitude of contraction or fractional shortening. Figure labels: No DNA: no DNA with lipofectamine, Control: 5-mer control DNA (SEQ ID NO:1), 80-mer: 80 nucleotide ssDNA (SEQ ID NO:8), 40-mer: 40 nucleotide ssDNA (SEQ ID NO:9), No Lipo 80-mer: 80 nucleotide ssDNA without lipofectamine.
Figure 9:
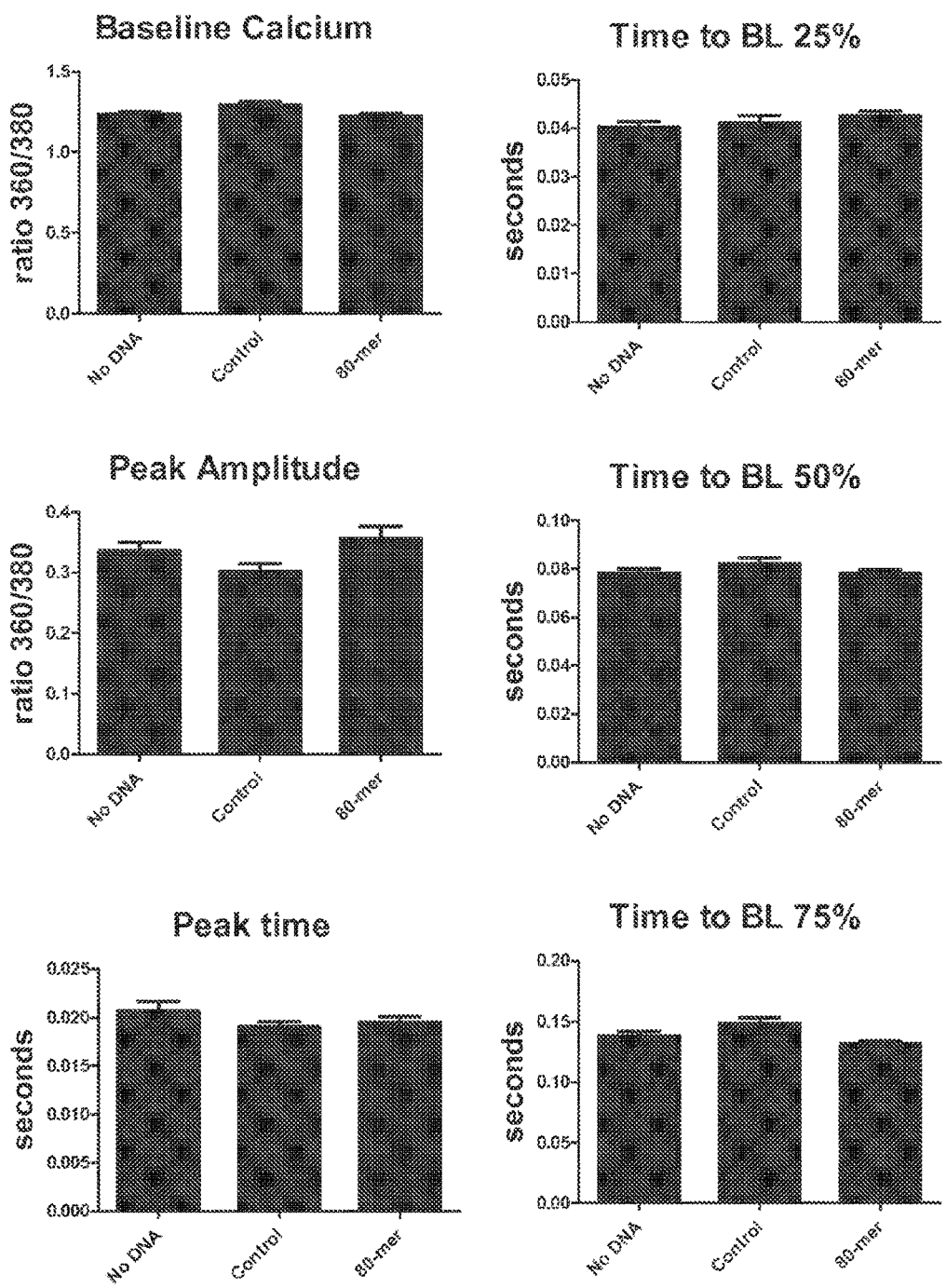
FIG. 9. Calcium transient dynamics reveal ssDNA has no effect on calcium cycling. ssDNA 80-mer does not alter any parameter of calcium transient analysis including peak amplitude of the calcium transient or in time to baseline at any time point. With the sarcomere length changes this suggests that the relaxation effect of ssDNA is calcium independent.

Two hours after transfection, 100 nM ssDNA 80-mer and 40-mer showed decreased Peak time and times to BL 25% and 50% while showing no change in Peak amplitude or fractional shortening (FIG. 8). This effect is not seen with the control DNA (5-mer) or without Lipofectamine for transfection. This result indicates that single stranded DNA increases the relaxation of adult cardiac myocytes without affecting the contractility. To determine if this effect on sarcomere length dynamics was due to changes in calcium we monitored calcium transient dynamics with the fluorescent indicator Fura-2 (FIG. 9). In relation to the control DNA (5-mer) or no DNA the 80-mer ssDNA has no effect on calcium transient dynamics. Taken together with the sarcomere length data this suggests that ssDNA increases relaxation in a calcium independent manner.

Figure 10:
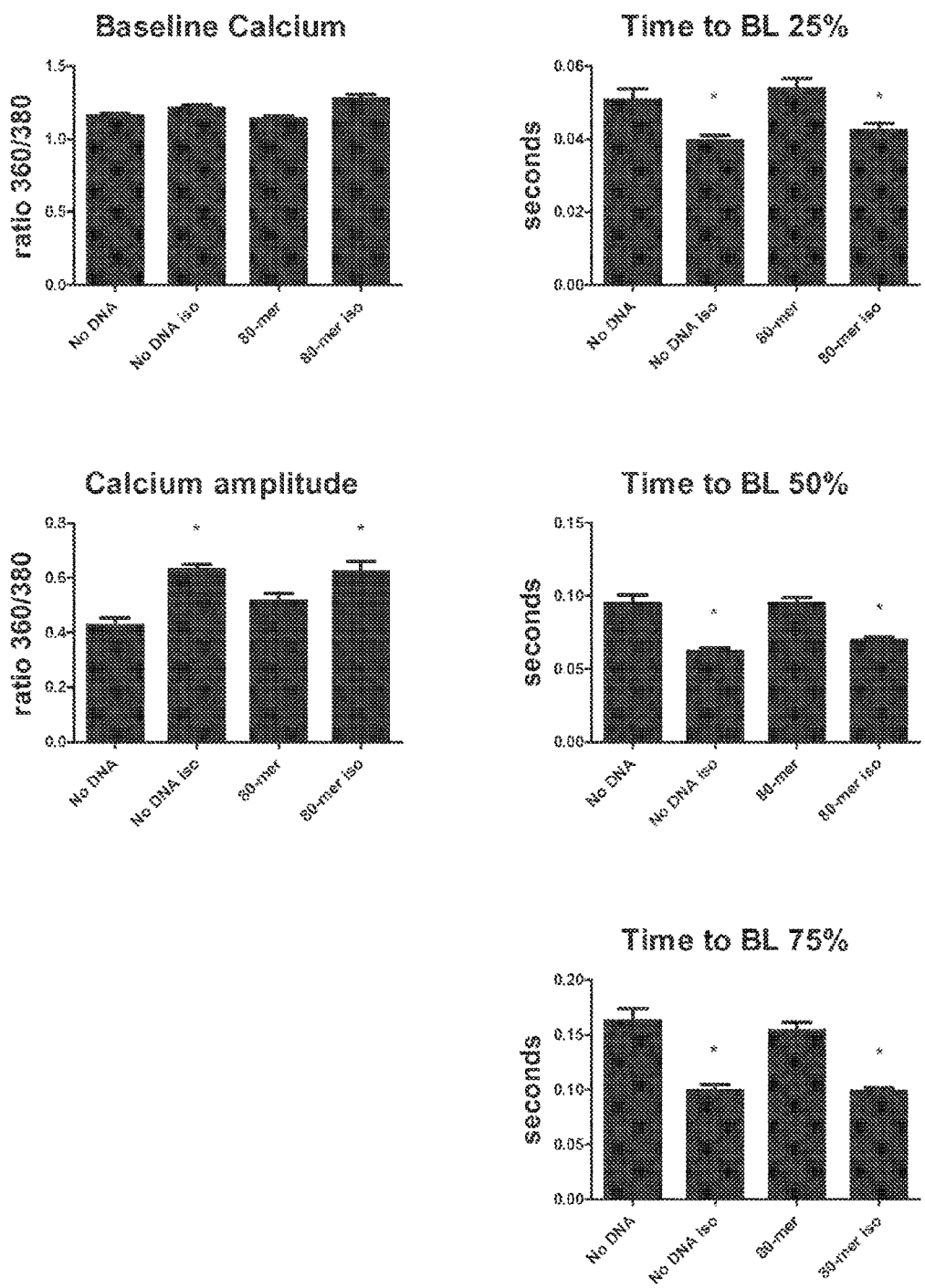
FIG. 10. Calcium transient dynamics +/−isoproterenol (iso). 10 nM isoproterenol results in increased calcium transient amplitude and decreased times to baseline in the presence and absence of ssDNA 80-mer. There is no difference in any parameter of calcium transient analysis with ssDNA 80-mer with or without isoproterenol.
Figure 11:
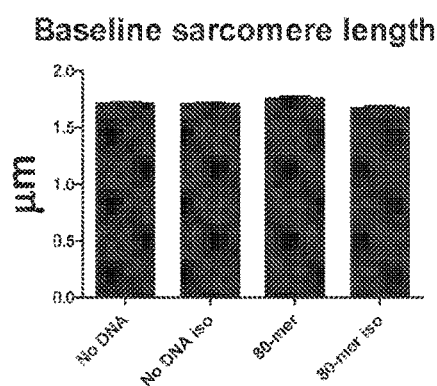
FIG. 11. Sarcomere length dynamics +/−isoproterenol (iso). 10 nM isoproterenol results in increased peak amplitude of contraction as well as decreased times to baseline in the presence and absence of ssDNA 80-mer. ssDNA 80-mer does decrease times to baseline at 25% and 50% without isoproterenol but has no effect with isoproterenol.
Figure 11:
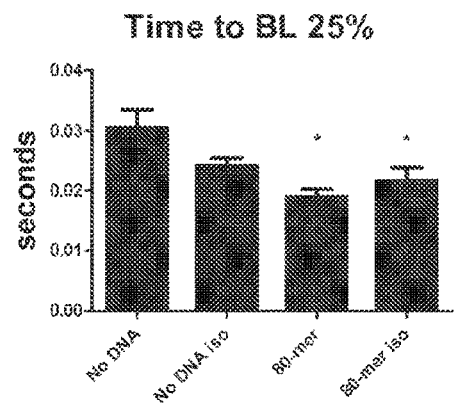
Figure 11:
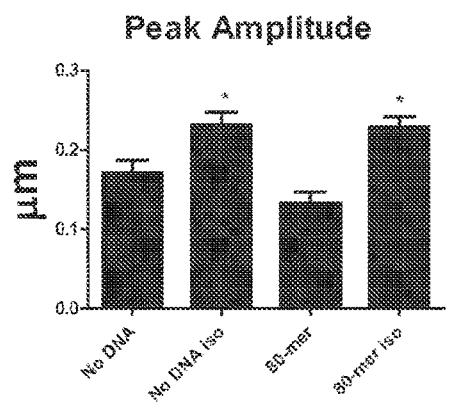
Figure 11:
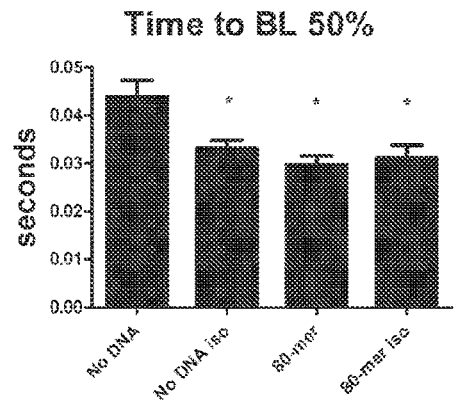
Figure 11:
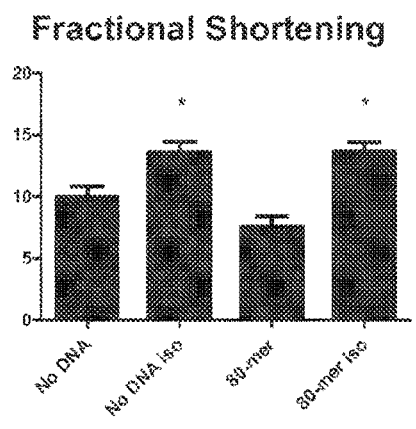
Figure 11:
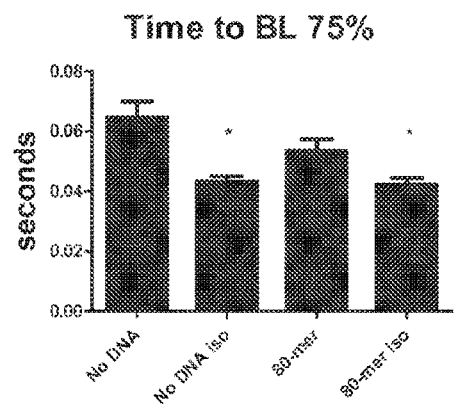

As two of the ssDNA binding proteins shown here are downstream targets of β-adrenergic signaling and regulators of increased contractility and relaxation with β-adrenergic stimulation, we investigated the impact of ssDNA with isoproterenol stimulation. Isoproterenol stimulation resulted in increased peak amplitude of contraction as well as decreased times to BL 50% and 75% (FIG. 11). This is attributed to the increased calcium peak amplitude and decreased time to BL 50% and 75% for calcium transient dynamics (FIG. 10). 80-mer ssDNA showed decreased time to BL 25% and 50% with no alterations in calcium transient kinetics. In the presence of isoproterenol, 80-mer ssDNA had no additional effect. This result may be an indication that the relaxation performance is maximized and/or that the relaxation effect of ssDNA is in the same pathway as isoproterenol signaling. These data also indicate that ssDNA does not result in a phenocopy of isoproterenol stimulation, suggesting that ssDNA only hits part of this pathway or mechanistically is independent of this pathway.

Figure 15:
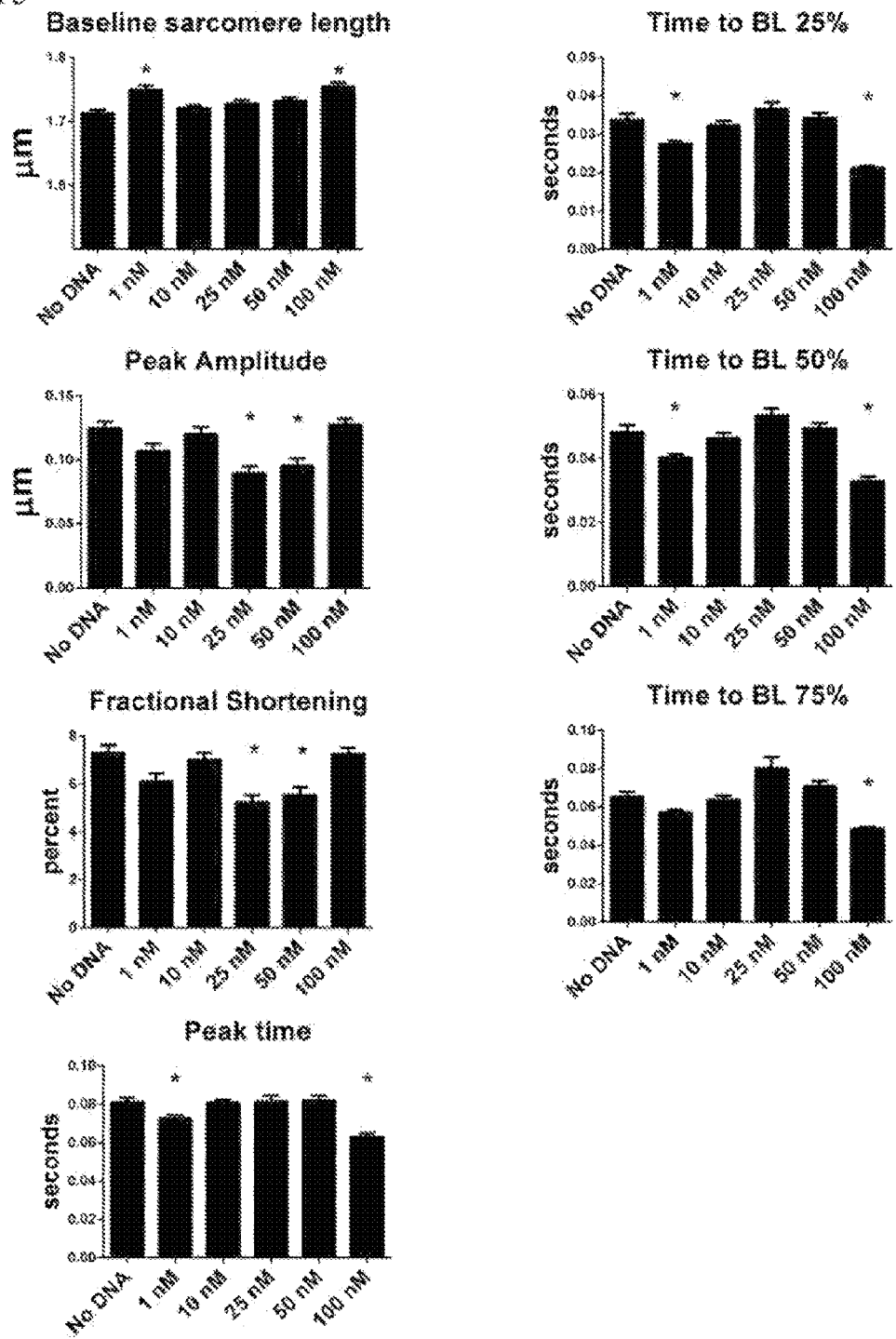
FIG. 15. Concentration dependence of sarcomere relaxation in adult cardiac myocytes. 80-mer ssDNA (SEQ ID NO:8) at varying concentrations (nM) was transfected into rat ventricular adult cardiac myocytes and sarcomere length dynamics were collected. 100 nM concentration decreases time to peak and time to baseline 25% and 50% indicative of increasing relaxation. 1 nM also statistically alters relaxation but to a lesser degree than 100 nM. 10-50 nM has no effect on relaxation parameters but 25 and 50 nM have decreased contractility. This data suggests 100 nM ssDNA is necessary for the cellular relaxation effect. *=P<0.05 by one way ANOVA.

The dependence of adult cardiac myocyte function on ssDNA concentration was evaluated with 80-mer ssDNA at varying concentrations. As is shown in FIG. 15, 100 nM ssDNA was necessary to see the full effect in times to BL 25% and 50% as well as peak time. Therefore, in the cellular context with the transfection protocol used here, 100 nM ssDNA is the lower limit for a cellular phenotype.

Figure 16:
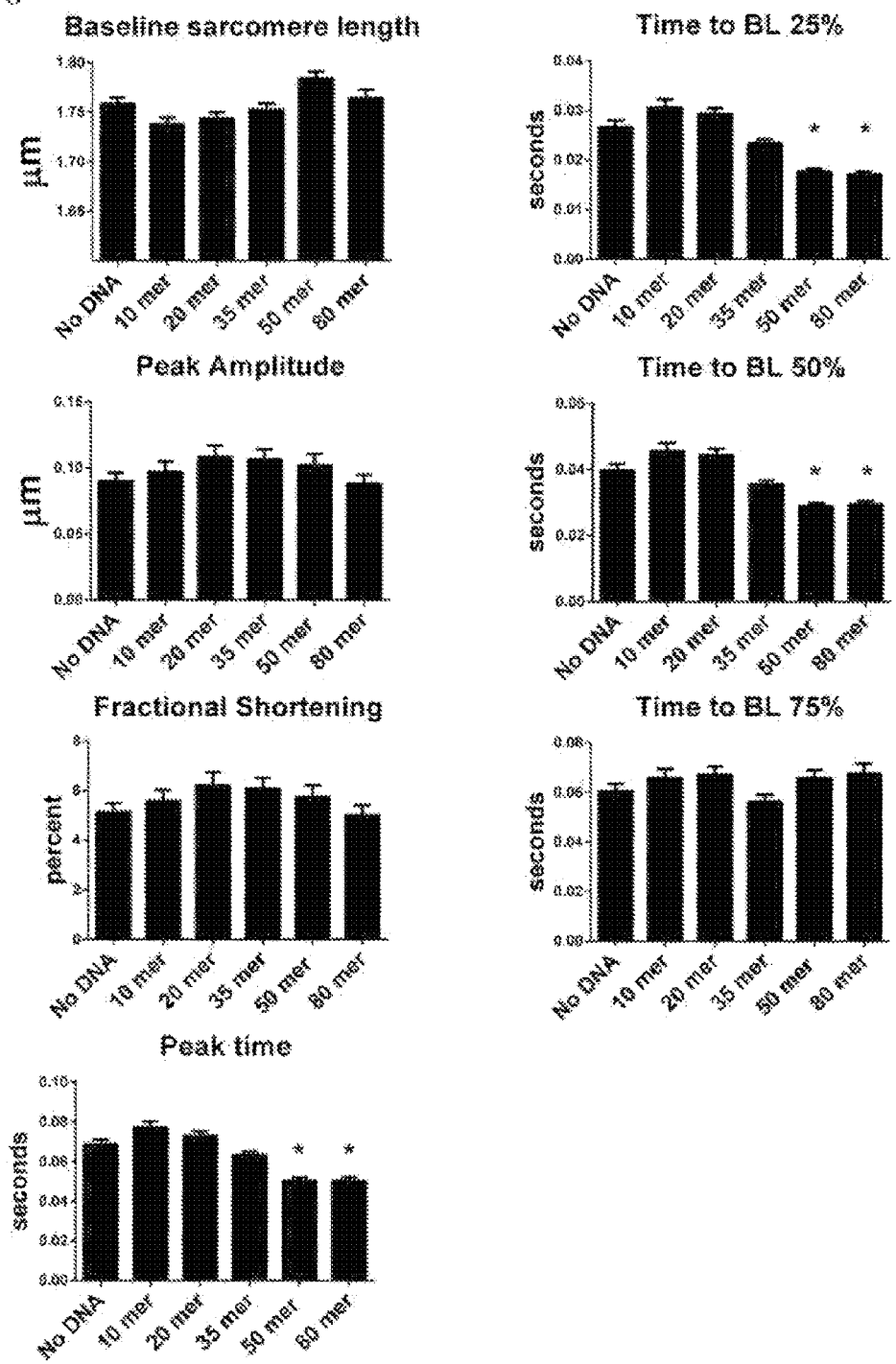
FIG. 16. Length dependence of random sequence ssDNA on sarcomere relaxation in adult cardiac myocytes. Completely random sequence ssDNA of varying length at 100 nM was transfected into rat ventricular adult cardiac myocytes and sarcomere length dynamics were collected. 50-mer and 80-mer show decreased peak time and time to baseline 25% and 50%. 35-mer shows a slight trend but does not statistically alter sarcomere length dynamics. With the other data presented here at least 40 nucleotides are necessary for the cellular effect of enhanced relaxation. *=P<0.05 by one way ANOVA.

The dependence of adult cardiac myocyte function on ssDNA length was evaluated through transfection of random sequence ssDNA of varying length at 100 nM concentration. As is shown in FIG. 16, 50-mer ssDNA was necessary for the full effect of decreasing time to BL 25% and 50% as well as peak time. These data, taken with the data from FIG. 8 (showing a 40-mer results in the same phenotype), suggest that 40 nucleotides are necessary for the full ssDNA effect of relaxation enhancement.

Figure 20:
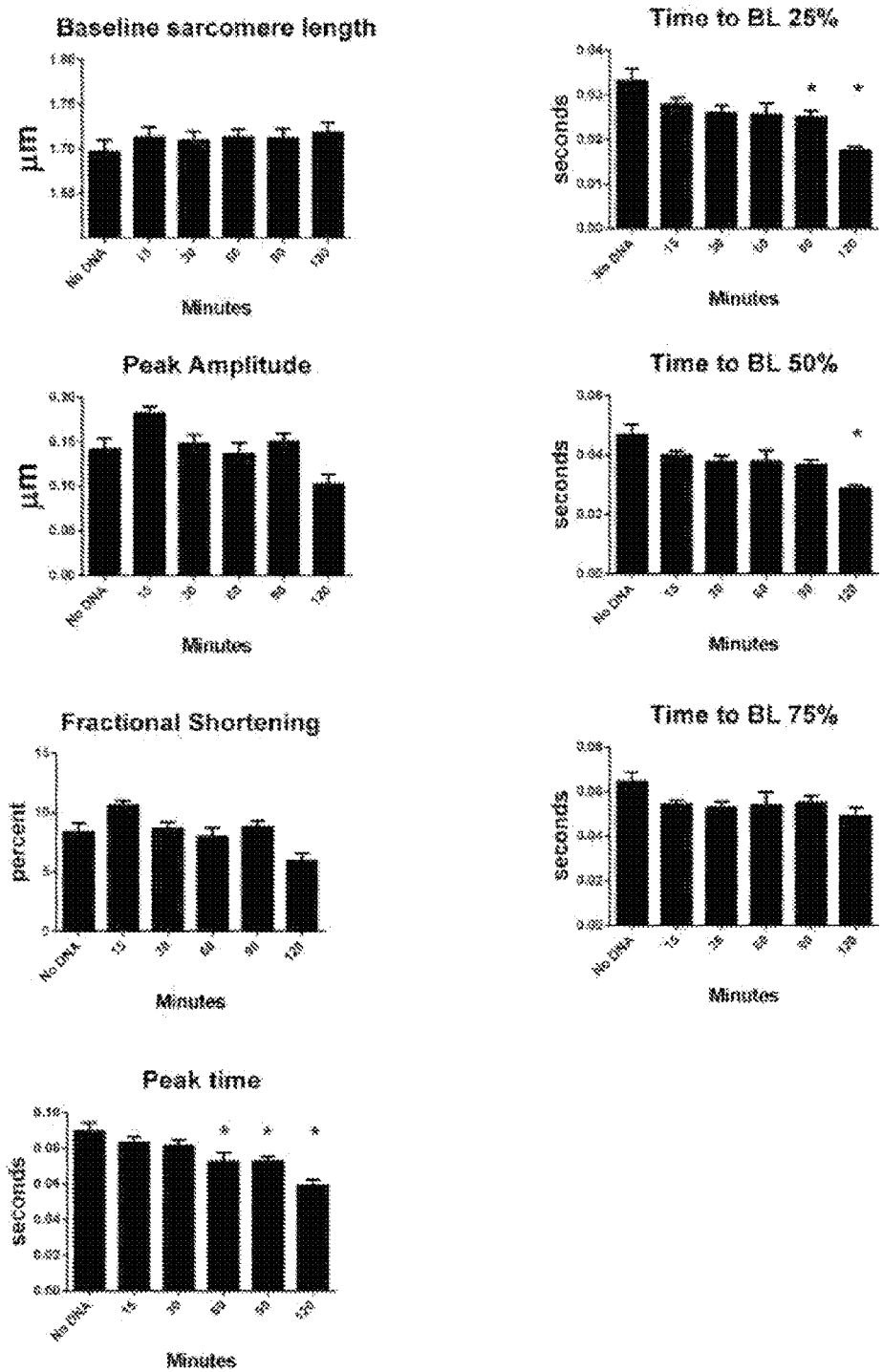
FIG. 20. ssDNA time dependence for transfection. ssDNA random 50-mer was transfected at 100 nM into adult cardiac myocytes and sarcomere dynamics were analyzed at varying time points after transfection. Only 120 minutes shows the full phenotype of reduced time to BL 25% and 50% along with reduced peak time. 60 and 90 minutes show a partial phenotype of decreased peak time and trends to decreased time to BL 25% and 50%. Data was collected from two independent myocyte preparations with an N=15-20 myocytes. *=P<0.05 by one way ANOVA.

The dependence of adult cardiac myocyte function on time following ssDNA transfection was evaluated by transfecting 100 nM random 50-mer ssDNA into adult cardiac myocytes and function analyzed at the stated times after transfection. As shown in FIG. 20, 120 minutes is necessary for the full ssDNA effect of decreased peak time and time to BL 25% and 50%. 60 minutes and 90 minutes gives an intermediate phenotype. All of this together suggests that with the present transfection protocol, 40 nucleotides at 100 nM for two hours of transfection is necessary for the full effect of ssDNA in adult cardiac myocytes.

Figure 17:
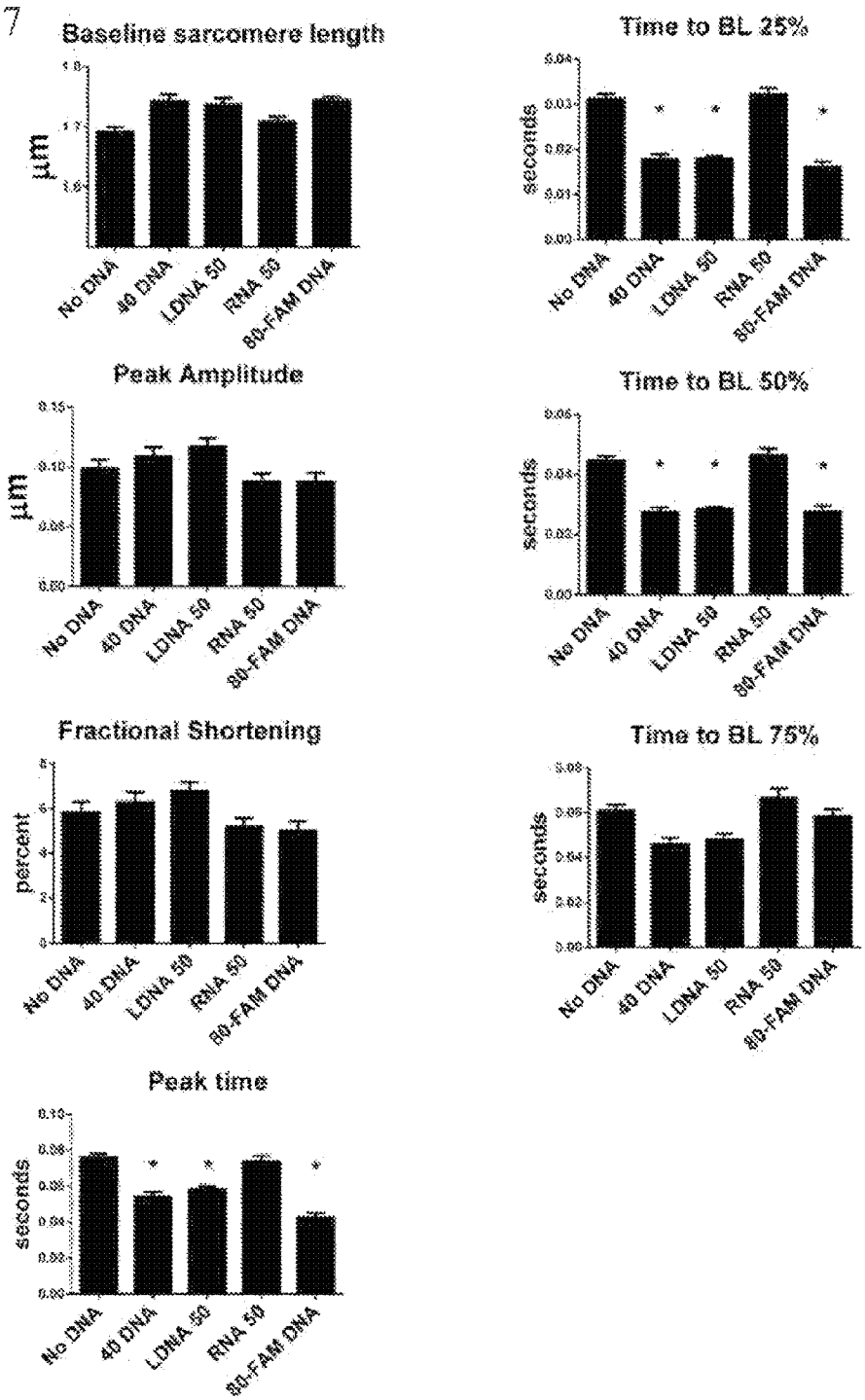
FIG. 17. Random 50-mer L-DNA and RNA comparison on sarcomere relaxation in adult cardiac myocytes. Completely random 50-mer enantiomer L-DNA, 40-mer ssDNA (SEQ ID NO:9), or 80-mer fluorescently labeled (80-FAM, SEQ ID NO:8) was transfected into rat ventricular adult cardiac myocytes and sarcomere length dynamics were collected. As shown previously 40-mer and 80-FAM show decreased peak time and time to BL 25% and 50%. L-DNA shows the same phenotype of increased relaxation while RNA under the conditions utilized shows no effect on sarcomere length dynamics. *=P<0.05 by one way ANOVA.
Figure 18:
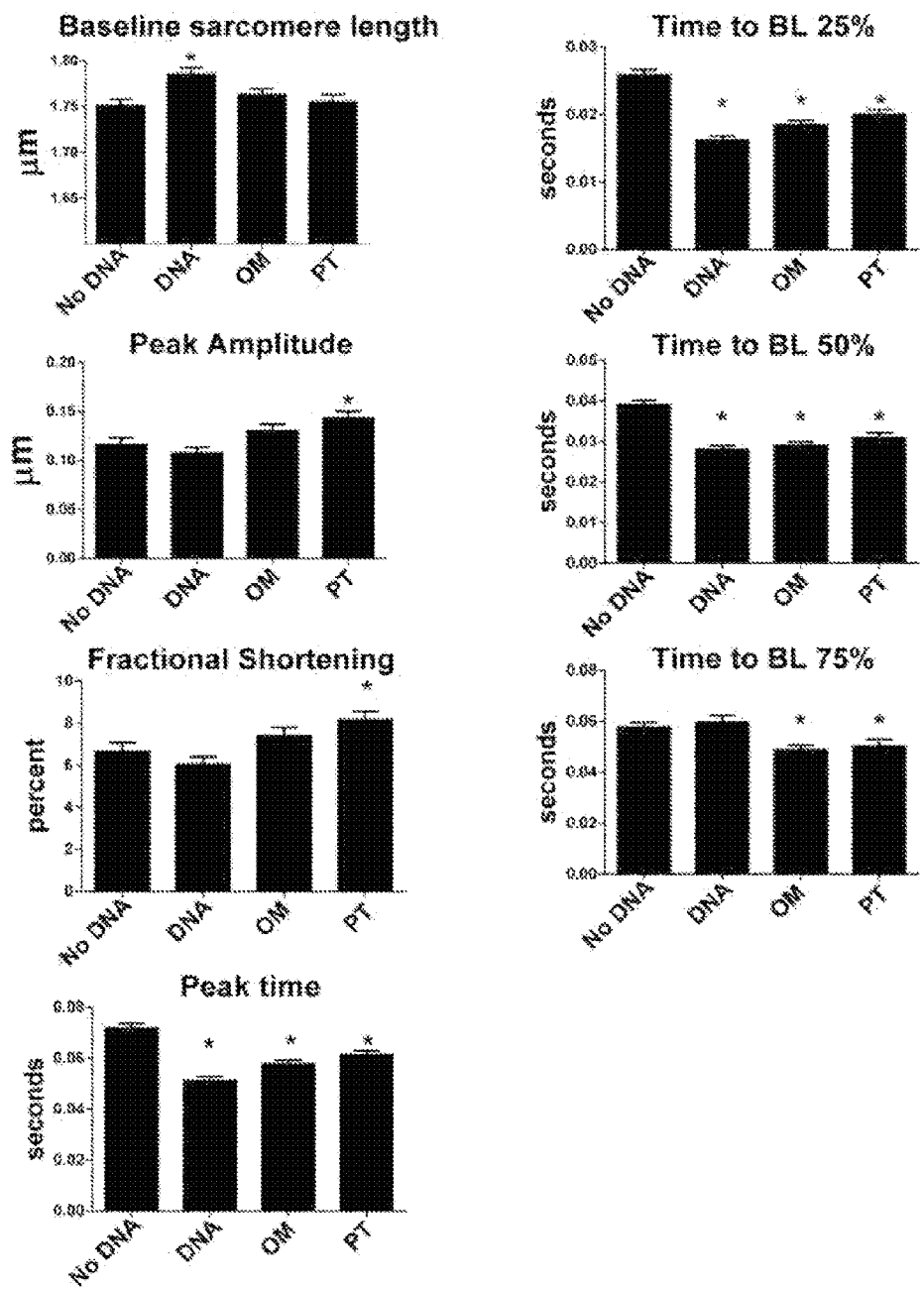
FIG. 18. Random 50-mer DNA, phosphorothioate DNA (PT), and 2'-O-methyl RNA (OM) comparison on sarcomere relaxation in adult cardiac myocytes. 50-mer ssDNA (100 nM), PT DNA (100 nM) or OM RNA (200 nM) was transfected into rat ventricular adult cardiac myocytes and sarcomere length dynamics were collected. All three nucleotide moieties show decreased peak time and time to BL 25% and 50%. PT and OM also show decreased time to BL 75%. PT DNA also shows enhanced peak amplitude of contraction suggesting that this moiety has slightly different effects from the other nucleotide moieties tested. *=P<0.05 by one way ANOVA.

To further characterize the effect of ssDNA in adult cardiac myocytes we used different moieties of oligonucleotides. All moieties tested were 50-mer of random sequence at 100 nM (with exception of OMRNA at 200 nM) for two hours of transfection. L-DNA is the enantiomer of ssDNA, PT-DNA is phophorothioate backbone DNA and OM-RNA is 2'-o-methyl RNA. As shown in FIG. 17 and FIG. 18, L-DNA, PT-DNA and Om-RNA have the same effect on relaxation as random 50-mer ssDNA, decreasing time to BL 25% and 50%. In addition, PT-DNA has a contractility phenotype of increasing peak amplitude of contraction and fractional shortening. This suggests that PT-DNA may have additional effects compared to ssDNA and/or may have alternate targets.

Figure 19:
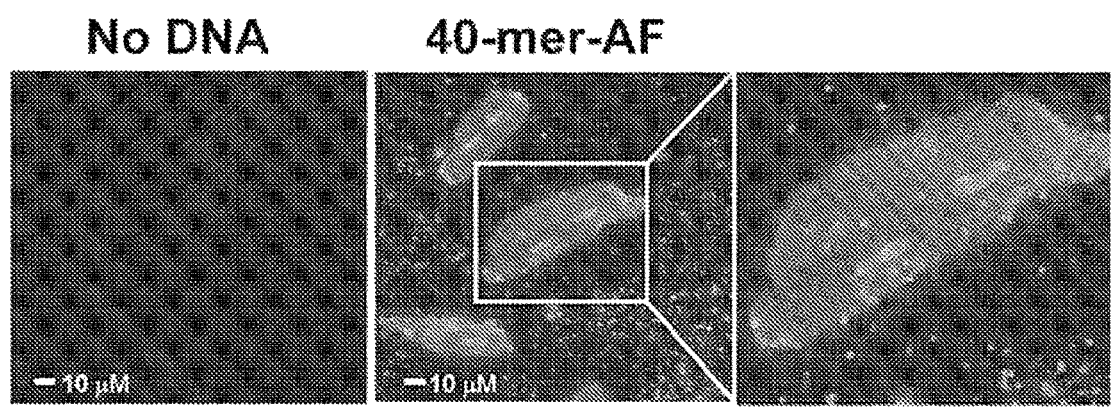
FIG. 19. Immunofluorescence of 40-mer-AF ssDNA. 40-mer ssDNA labeled with Alexafluor 594 was transfected at 100 nM for two hours into adult ventricular cardiac myocytes. Cells were then treated with blebbistatin to preserve morphology and permeabilized and fixed. Confocal microscopy was used to visualize the fluorescence at 40×. No DNA served as a control. 40-mer-AF shows prominent nuclear staining as well as cytosolic staining that is striated in nature.

In addition to cellular function we provide evidence that ssDNA 40-mer-AF is present in the cytosol of adult cardiac myocytes. FIG. 19 shows immunofluorescence of 40-mer-AF two hours after transfection. Nuclear staining is prominent while the cytosolic staining is apparent and is striated in nature. This striated pattern is consistent with a sarcomeric staining pattern.

In total, the cellular data suggests that ssDNA moieties of completely random sequence have the potential to improve diastolic function in the heart independent of calcium handling changes. Improving diastolic function is of major importance as diastolic heart failure is a growing problem, representing approximately 40% of heart failure cases. Diastolic heart failure is defined as heart failure with preserved systolic function and is characterized by decreased ability to fill the heart with blood during diastole. Our present data suggest that ssDNA therapy could improve this cohort of patients through calcium independent enhanced relaxation which would allow the heart to fill with blood more appropriately.

Thus, in one aspect, we describe a composition that includes an xNA molecule having a length of at least six nucleotides, in an amount effective to improve at least one indicator of myocyte function.

In some embodiments, the composition can further include a pharmaceutically acceptable carrier. The composition described herein may be formulated in a composition along with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. By "pharmaceutically acceptable" is meant that the carrier is not biologically or otherwise undesirable, i.e., the carrier may be administered to an individual along with the xNA without causing any undesirable biological effects or interacting in a deleterious manner with any of the other components of the pharmaceutical composition in which it is contained. In some embodiments, the pharmaceutical carrier may be particularly selected for delivering the xNA to cardiac tissue.

The xNA may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). It is foreseen that a composition can be administered to a mucosal surface, such as by administration to, for example, the nasal or respiratory mucosa (e.g., by spray or aerosol). A composition also can be administered via a sustained or delayed release. In certain specific embodiments, the composition may be delivered intravenously, intraperitoneally, or subcutaneously.

A formulation may be conveniently presented in unit dosage form and may be prepared by methods well known in the art of pharmacy. Methods of preparing a composition with a pharmaceutically acceptable carrier include the step of bringing the xNA into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

In some embodiments, the xNA may be linear or circular in topology. The xNA may be in any form suitable for transfection into a cell including, for example, naked DNA or a component or portion of a vector that can provide for further cloning (e.g., a cloning vector) and/or may function in multiple hosts (e.g., a shuttle vector). A vector may include, but is not limited to, plasmid, phagemid, F-factor, virus, cosmid, or phage. Exemplary viral vectors include Ad5, rAAV, and Lentivirus vectors. The vector may be in a double-stranded or single-stranded linear or circular form. The vector can also transform a prokaryotic or eukaryotic host either by integrating into the cellular genome or by existing extrachromosomally (e.g., as an autonomous replicating plasmid with an origin of replication). Methods for introducing an xNA into a vector are well known in the art (Sambrook et al., Molecular Cloning: A Laboratory Manual, 3rd edition, Cold Spring Harbor Press, Cold Spring Harbor, N.Y. (2001)).

The amount of xNA administered can vary depending on various factors including, but not limited to, the specific xNA, the weight, physical condition, and/or age of the subject, and/or the route of administration. Thus, the absolute amount of xNA included in a given unit dosage form can vary widely, and depends upon factors such as the species, age, weight and physical condition of the subject, as well as the method of administration. Accordingly, it is not practical to set forth generally the amount that constitutes an amount of xNA effective for all possible applications. Those of ordinary skill in the art, however, can readily determine the appropriate amount with due consideration of such factors.

In some embodiments, the method can include administering sufficient xNA to provide a dose of, for example, from about 100 ng/kg to about 50 mg/kg to the subject, although in some embodiments the methods may be performed by administering xNA in a dose outside this range. In some of these embodiments, the method includes administering sufficient xNA to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area (m²) is calculated prior to the beginning of the treatment course using the Dubois method: $m^2 = (wt\ kg^{0.425} \times height\ cm^{0.725}) \times 0.007184$.

In some embodiments, the method can include administering sufficient xNA to provide a dose of, for example, from about 0.01 mg/m² to about 10 mg/m².

In some embodiments, an xNA may be administered, for example, from a single dose to multiple doses per week, although in some embodiments the method can be performed by administering an xNA at a frequency outside this range. In certain embodiments, the xNA may be administered from about once per month to about five times per week.

The xNA may be of any suitable predetermined length. In some embodiments, the length of the xNA can be no less than a minimum of six nucleotides in length such as, for example, no less than seven nucleotides, no less than eight nucleotides, no less than nine nucleotides, no less than ten nucleotides, no less than 11 nucleotides, no less than 12 nucleotides, no less than 13 nucleotides, no less than 14 nucleotides, no less than 15 nucleotides, no less than 16 nucleotides, no less than 17 nucleotides, no less than 18 nucleotides, no less than 19 nucleotides, no less than 20 nucleotides, no less than 21 nucleotides, no less than 22 nucleotides, no less than 23 nucleotides, no less than 23 nucleotides, no less than 24 nucleotides, no less than 25 nucleotides, no less than 26 nucleotides, no less than 27 nucleotides, no less than 28 nucleotides, no less than 29 nucleotides, no less than 30 nucleotides, no less than 31 nucleotides, no less than 32 nucleotides, no less than 33 nucleotides, no less than 34 nucleotides, no less than 35 nucleotides, no less than 36 nucleotides, no less than 37 nucleotides, no less than 38 nucleotides, no less than 39 nucleotides, no less than 40 nucleotides, no less than 41 nucleotides, no less than 42 nucleotides, no less than 43 nucleotides, no less than 44 nucleotides, no less than 45 nucleotides, no less than 46 nucleotides, no less than 47 nucleotides, no less than 48 nucleotides, no less than 49 nucleotides, no less than 50 nucleotides, no less than 51 nucleotides, no less than 52 nucleotides, no less than 53 nucleotides, no less than 54 nucleotides, no less than 55 nucleotides, no less than 56 nucleotides, no less than 57 nucleotides, no less than 58 nucleotides, no less than 59 nucleotides, no less than 60 nucleotides, no less than 61 nucleotides, no less than 62 nucleotides, no less than 63 nucleotides, no less than 64 nucleotides, no less than 65 nucleotides, no less than 66 nucleotides, no less than 67 nucleotides, no less than 68 nucleotides, no less than 69 nucleotides, no less than 70 nucleotides, no less than 71 nucleotides, no less than 72 nucleotides, no less than 73 nucleotides, no less than 74 nucleotides, no less than 75 nucleotides, no less than 76 nucleotides, no less than 77 nucleotides, no less than 78 nucleotides, no less than 79 nucleotides, or no less than 80 nucleotides.

In some embodiments, the length of the xNA can be no more than a maximum of 80 nucleotides such as, for example, no more than 79 nucleotides, no more than 78 nucleotides, no more than 77 nucleotides, no more than 76 nucleotides, no more than 75 nucleotides, no more than 74 nucleotides, no more than 73 nucleotides, no more than 72 nucleotides, no more than 71 nucleotides, no more than 70 nucleotides, no more than 69 nucleotides, no more than 68 nucleotides, no more than 67 nucleotides, no more than 66 nucleotides, no more than 65 nucleotides, no more than 64 nucleotides, no more than 63 nucleotides, no more than 62 nucleotides, no more than 61 nucleotides, no more than 60 nucleotides, no more than 59 nucleotides, no more than 58 nucleotides, no more than 57 nucleotides, no more than 56 nucleotides, no more than 55 nucleotides, no more than 54 nucleotides, no more than 53 nucleotides, no more than 52 nucleotides, no more than 51 nucleotides, no more than 50 nucleotides, no more than 49 nucleotides, no more than 48 nucleotides, no more than 47 nucleotides, no more than 46 nucleotides, no more than 45 nucleotides, no more than 44 nucleotides, no more than 43 nucleotides, no more than 42 nucleotides, no more than 41 nucleotides, no more than 40 nucleotides, no more than 39 nucleotides, no more than 38 nucleotides, no more than 37 nucleotides, no more than 36 nucleotides, no more than 35 nucleotides, no more than 34 nucleotides, no more than 33 nucleotides, no more than 32 nucleotides, no more than 31 nucleotides, no more than 30 nucleotides, no more than 29 nucleotides, no more than 28 nucleotides, no more than 27 nucleotides, no more than 26 nucleotides, no more than 25 nucleotides, no more than 24 nucleotides, no more than 23 nucleotides, no more than 22 nucleotides, no more than 21 nucleotides, no more than 20 nucleotides, no more than 19 nucleotides, no more than 18 nucleotides, no more than 17 nucleotides, no more than 16 nucleotides, no more than 15 nucleotides, no more than 14 nucleotides, no more than 13 nucleotides, no more than 12 nucleotides, no more than 11 nucleotides, no more than ten nucleotides, no more than nine nucleotides, no more than eight nucleotides, or no more than seven nucleotides.

The length of the xNA also can be characterized by any range that includes, as endpoints, any combination of a minimum length identified above and any maximum length identified above that is greater than the minimum length. For example, in some embodiments, the length of the xNA can range from at least 5 nucleotides to no more than 80 nucleotides. As another example, the length of the xNA can range from at least 5 nucleotides to no more than 30 nucleotides.

In some embodiments, the indicator of myocyte function can include relaxation. In such cases, an improvement of myocyte relaxation can include reducing the time required to return to baseline after contraction. Other indicators of improved myocyte function can include, for example, LV tau, −dP/dt, LV end diastolic pressure.

In another aspect, we disclose a method for treating cardiac disease. Generally, the method includes administering to a subject a composition that includes an xNA molecule having a length of at least six nucleotides in an amount effective to improve at least one indicator of myocyte function. In some embodiments, the composition can further includes a pharmaceutically acceptable carrier as described herein.

In yet another aspect, we disclose a method of tuning treatment of cardiac disease. Generally, the method includes evaluating the efficacy of treatment of cardiac disease in which a subject is being treated with a first xNA molecule that has a predetermined length. If treatment with the first xNA is insufficient, the method includes administering to the subject a second xNA molecule that is longer than the first xNA molecule. If, however, treatment with the first xNA is too potent, the method includes administering to the subject a second xNA molecule that is shorter than the first xNA molecule.

In some embodiments, evaluating the efficacy of treatment using the first xNA molecule can include evaluating myocyte relaxation under treatment with the first xNA molecule.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

U-[$^{13}$C] labeled pentameric PLN was expressed as a fusion protein with maltose-binding protein and purified as described previously (Buck et al., *Protein Expr. Pur* 30:253-261 (2003)). SERCA1a isoform was extracted from rabbit skeletal muscle, purified, and tested for activity as reported previously (Ha et al., *J. Biol. Chem.* 282:37205-37214 (2007)). Lipids were purchased from Avanti (Alabaster, Ala.). Nuclease free H$_2$O and all single stranded DNA (ssDNA, Table 1) sequences were purchased from Integrated DNA Technologies, Inc. (Coralville, Iowa).

All chemicals were from Sigma Aldrich (St. Louis, Mo.) at the highest grade available, except MgCl$_2$ (99.8%, Mallinckrodt Baker), KCl (99.5%, Mallinckrodt Baker), CaCl$_2$ (99.9%, Mallinckrodt Baker), NaCl (99.0%, Spectrum), 3-Morpholinopropanesul-fonic acid (MOPS, 99.5%, Fluka Analytical), and DL-Dithiothreitol (DTT, 99.0%, MP Biomedicals). Binding buffer and separation buffer were made in nuclease free H$_2$O and filtered through a 0.2 μm membrane filter before use. Binding buffer contained 20 mM MOPS, 0.1% (w/v) Octaethylene glycol monododecyl ether (C$_{12}$E$_8$), 0.25 mM DTT, 1 mM MgCl$_2$, 1 mM KCl, and 5 mM CaCl$_2$ at pH 7.0 (pH adjusted by 1M NaOH). Separation buffer consists of 20 mM MOPS and 0.1% (w/v) C$_{12}$E$_8$ at pH 7.0 (pH adjusted by 1M NaOH).

SERCA Activity Assays

The effect of oligonucleotide ligands on the inhibitory complex between SERCA and PLN were measured in dioleylphosphatidylcholine/dioleylphosphoetahnolamine (DOPC/DOPE) lipid vesicles. Recombinant PLN[15] was co-reconstituted in lipid membranes (DOPC:DOPE, 4:1) with SERCA purified from rabbit muscle[16] at molar ratios of 10:1 PLN:SERCA and 700:1 lipid:SERCA. A solution of ssDNA in deionized water was added directly to the vesicles at a molar ratio of 10:1:1 SERCA:PLN:ssDNA and incubated for 20 minutes at 25° C. prior to starting the assay. The calcium dependence of the SERCA activity was measured at 25° C. using a coupled enzyme assay[17]. The consumption of NADH was monitored as a decrease in UV absorbance at 340 nm using a Spectromax microplate reader (Molecular Devices). The initial ATPase rate (V) was measured as a function of pCa, and the data were fit using the Hill equation:

$$V = V_{max}/[1+10^{n(pK_{Ca}-pCa)}] \qquad (1)$$

to determine $V_{max}$, $pK_{Ca}$ (the pCa value where $V=V_{max}/2$), and n (Hill coefficient). $V_{max}$ was obtained from the fit, and the data were plotted as $V/V_{max}$ versus pCa. Results are expressed as changes in $pK_{Ca}$.

Preparation of Pig Cardiac SR Vesicles and SERCA Activity Assay

Pig cardiac SR vesicles were prepared as reported previously (Ablorh et al., *Anal. Biochem.* 425:68-75 (2012)). Briefly, the ventricle of a pig heart (Lindenfelser's Meats, Monticello, Minn., USA) was extracted and placed on ice within 10 seconds of sacrifice. Ventricle tissue was homogenized in extraction buffer (10 mM NaHCO$_3$, 10 mM Tris-HCl (pH to 7.2 with KOH), 0.8 M benzamidine, 0.1 μg/mL aprotinin, 0.1 μg/mL leupeptin, 1 M phenylmethanesulfonyl fluoride (PMSF), and 0.1 μg/mL pepstatin) and centrifuged at 4° C. for 20 minutes at 11,000 g. The supernatant was filtered and incubated for one hour in 0.6 M KCl solution. After centrifugation at 4° C. for 45 minutes at 100,000 g, the pellet was resuspended in 15 mL of sucrose buffer (10% sucrose, 20 mM MOPS, 1 mM NaN$_3$, 25 g/L aprotinin, 25 g/L leupeptin, 50 g/L benzamidine, 0.1 M PMSF and 0.1 g/mL pepstatin A; pH adjusted to 7.00 with KOH) and centrifuged again for 45 minutes at 100,000 g. The pellet was resuspended in sucrose solution.

SR vesicles were used directly to assay SERCA2a activity in the presence and absence of ssDNA. Two microliters of pig cardiac SR vesicles were used for each assay (corresponding to ~20 μg of total SR proteins as determined by bicinchoninic acid assay) and incubated in a final volume of 100 μL with 1 μM of ssDNA (80-mer) for 30 minutes prior to measurements. All data were acquired and processed as described in the previous section.

NMR Sample Preparation

Magic angle spinning samples were prepared by mixing 10 mg of DMPC lipids with 2 mg of recombinant [U-$^{13}$C]-PLN in 500 μL of chloroform. The mixture was dried under a stream of nitrogen gas and desiccated overnight. To rehydrate the lipid/protein film, a buffer containing 20 mM MOPS and 100 mM NaCl at pH 7.0 was added to a final volume of 1 mL. The suspension was vortexed and briefly sonicated in order to generate PLN-containing multi-lamellar lipid vesicles (MLVs). The mixture was lyophilized, re-suspended in 10 μL of ddH$_2$O and transferred to a 3.2 mm thin wall rotor MAS rotor. The final samples contained approximately 50% H$_2$O with a lipid:PLN ratio of 300:1.

Isotropic bicelle samples for solution NMR were prepared by dissolving 1 mg of [U-$^{13}$C, $^{15}$N] PLN in a solution of DHPC (174 mg/mL) containing 20 mM MOPS, 100 mM NaCl, and 5% D$_2$O. The protein/DHPC solution was transferred to lyophilized DMPC (21.9 mg) lipids, vortexed and sonicated extensively. Several freeze/thaw cycles were needed to form a clear solution. Final DMPC:DHPC molar ratio (q) was 0.33. Finally, the protein/bicelles solution transferred to a 5 mm Shighemi tube.

NMR Experiments

All NMR experiments were performed on a VNMRS spectrometer operating at a proton frequency of 600 MHz. One-dimensional $^{13}$C-carbon spectra were acquired using a cross-polarization (CP) of 1 ms and spectral width of 100 kHz. The sample was spun at 8 kHz and the temperature was 25° C. Chemical shifts in MLVs were assigned using refocused Insensitive Nuclei Enhanced by Polarization Transfer (rINEPT) experiments acquired using a $^1$H/$^{13}$C magic angle spinning probe. Pulse widths were 5.5 μs ($^{13}$C, $^{15}$N), 2.5 μs ($^1$H) and a 100 kHz $^1$H decoupling field strength was used. Chemical shifts were referenced to the $^{13}$C signal of adamantane (40.48 ppm). Spectral widths of 100 kHz and 3.33 kHz were used in the direct and indirect $^{13}$C dimensions, respectively. A total of 640 scans with 30 increments in the indirect dimension were required to achieve desired sensitivity and peak resolution. Sample spinning rate was 8 kHz. Data were processed using NMRPipe and analyzed with NMRview5 software.

Affinity Capillary Electrophoresis (ACE)

All ACE experiments were performed on a commercial CE system (P/ACE MDQ, Beckman Coulter, Inc., Fullerton, Calif.) with laser induced fluorescence (LIF) detection ($\lambda_{ex}$=488 nm, $\lambda_{em}$=520 nm). Fluorescently labeled ssDNA samples (2.5 nM) were titrated with increasing concentrations of PLN. The mixtures were then injected into a 50 cm long, 50 μm inner diameter fused silica capillary (Polymicro Technologies, Phoenix, Ariz.) using hydrodynamic injection at 1 psi for 4 seconds. All separations were performed at 30 kV for 10 min. Electropherograms were analyzed using Cutter 7.0, and peak heights of the free ssDNA peaks were used to calculate the bound fractions. $K_d$ values were obtained using the following equation (Haynes, S. R. in *RNA—protein interaction protocols* 481 (Humana Press, Totowa, N. J., 1999)):

$$f_a = \frac{c}{1 + \dfrac{K_d}{\left([P]_t - 0.5\left(\dfrac{[D]_t + [P]_t + K_d - }{(([D]_t + [P]_t + K_d)^2 - 4[D]_t[P]_t)^{0.5}}\right)\right)}} \quad (2)$$

where $f_a$ represents the bound fraction, c, $[P]_t$, and $[D]_t$ are maximum bound fraction, total PLN concentration, and total DNA concentration, respectively. $[P]_t$−0.5($[D]_t$+$[P]_t$+$K_d$−$(([D]_t$+$[P]_t$+$K_d)^2$−$4[D]_t[P]_t)^{0.5}$) represents the free concentration of PLN.

Fluorescence Polarization (FP)

All FP experiments were performed on a Synergy™ 2 Microplate Reader (BioTek Instruments, Inc., Winooski, Vt.) with similar filter settings ($\lambda_{ex}$=485±20 nm, $\lambda_{em}$=528±20 nm). Samples were prepared similarly to those assayed using ACE, and 15 μL aliquots of mixtures were loaded into a corning 3540 microplate (Corning Incorporated, Corning, N.Y.). Both parallel and perpendicular fluorescence intensities were collected to calculate polarization values with the calibration of the g factor using Gen 5™ software (BioTek Instruments, Inc., Winooski, Vt.). Bound fractions were then determined using the equation:

$$f_a = \frac{P - P_o}{P_m - P_o} \quad (3)$$

where $f_a$ is the bound fraction, and P, $P_m$, and $P_o$ are measured polarizations of a sample, complex, and free ssDNA, respectively. $P_m$ was determined as the plateau polarization value in the presence of excess PLN. The overall fluorescence intensity of each sample was monitored while increasing the concentration of PLN, and bound fraction was modified according to a previous published method if the overall fluorescence intensity was positively or negatively biased (Wei et al., *Anal. Chem.* 65:3372-3377 (1993)).

Native Gel Mobility Shift Assay

Native TBE 10% (Tris-Borate-EDTA) gels were prepared as reported in (Onizuka et al Bios. Biotech. Biochem 2002). PLN was dissolved in binding buffer consisting in 0.1% $C_{12}E_8$, 20 mM Tris-HCl, pH 7.0, 1 mM MgCl$_2$ and incubated with fluorescein-labeled ssDNA for 20 min at 25° C. Samples were mixed at a 1:1 ratio with 2× loading buffer (Bromophenol blue, glycerol, Tris pH 7.0). Samples were run at 100V at 4° C. and subsequently imaged by exposure to UV light. Signals from the PLN/DNA complex were integrated using ImageJ densitometry software (National Institute of Mental Health, Bethesda, Md., USA). The $K_d$ was determined from the non-linear fitting of the signal absolute intensities versus PLN concentration.

Example 2

Ventricular Myocyte Isolation and Primary Culture

Adult rat ventricular myocyte isolation was performed as previously described (Herron et al., *Circ. Res.* 100:1182-1190 (2007); Davis et al., *Circ. Res.* 100:1494-1502 (2007)). Briefly, adult female rats were anaesthetized by inhalation of isoflurane followed by intraperitoneal injection of heparin (1500 U/kg) and Nembutal (162.5 U/kg). Following enzymatic digestion by retro-grade perfusion with collagenase and gentle trituration of the cardiac ventricles, cardiac myocytes were plated on laminin-coated glass coverslips ($2 \times 10^4$ myocytes/coverslip) and cultured in M199 media (Sigma, supplemented with 10 mmol/L glutathione, 26.2 mmol/L sodium bicarbonate, 0.02% bovine serum albumin, and 50 U/ml penicillin-streptomycin, with pH adjusted to 7.4, additionally insulin (5 µg/ml), transferrin (5 µg/ml) and selenite (5 ng/ml) (ITS) were added (Sigma I1884)). One hour after plating, nonadherent cells were removed and fresh M199 was applied.

ssDNA Transfection

Day one adult cardiomyocytes were transfected with ssDNA via Lipofectamine 2000 transfection reagent according to manufactures protocol (Invitrogen). ssDNA of varying length was mixed with 5 µl Lipofectamine 2000 and applied to the cells in 1 ml Optimem. The final concentration of ssDNA was 100 nM in all studies. The transfection was allowed to proceed for two hours and then fresh media was applied until functional measures were conducted. No DNA controls with Lipofectamine and no Lipofectamine controls with ssDNA were used to control for Lipofectamine effects.

```
ssDNA used:
80 mer:
                                          (SEQ ID NO: 8)
5'-TTGGGGAGGG GCACTGGGCA GTGTAATTTA CGAAAGCGAG

TTGGGGAGGG GCACTGGGCA GTGTAATTTA CGAAAGCGAG-3';

40-mer:
                                          (SEQ ID NO: 9)
5'-GTAGAGATTC GTATTTTGGG GAGAAGCGGC

CGGAAGCGGA-3';
```

Control DNA: 5 nucleotides: 5'-GCTTG-3' (SEQ ID NO:1);

50-mer: Randomized single-stranded DNA;

L-DNA: 50-mer random sequence single stranded enantiomeric DNA;

RNA: 50-mer random sequence single stranded RNA;

PTDNA: 50-mer random sequence phosphorothioate backbone single stranded DNA;

OMRNA: 50-mer random sequence of 2'-O-methyl RNA.

Contractility Measurements in Single Intact Myocytes

Sarcomere length dynamics and kinetics were performed as previously described (Herron et al., *Circ. Res.* 100:1182-1190 (2007); Davis et al., *Circ. Res.* 100:1494-1502 (2007)). Briefly, cover slips containing single isolated myocytes, day one after isolation, were placed on an inverted microscope (Nikon, Eclipse TE2000) and electrically stimulated at 1 Hz in a 37° C. media bath. Tyrode's Solution pH 7.4 (Calcium 1.8 mM) was used for the media bath. Sarcomere length recordings were collected (1000 Hz) using a CCD camera (MyoCam, IonOptix). Myocytes that did not follow the pacing protocol (0.2 Hz) were excluded. Sarcomere length shortening and relaxation kinetics were calculated using IonOptix software. For calcium measurements 2 µM Fura-2-AM was loaded into cells for 10 minutes at room temperature. The cells were then washed and visualized 15 minutes later to allow for de-esterification using IonOptix software. For isoproterenol stimulation, 10 nM isoproterenol in Tyrodes pH 7.4 was added to the cells and five minutes later calcium and sarcomere dynamics were measured simultaneously. For all experiments, two to five independent myocyte preps were used with N=15-60 myocytes analyzed in total.

Immunofluorescence of 40-Mer-AF 40-mer ssDNA labeled with Alexafluor 594 was transfected at 100 nM for two hours into adult ventricular cardiac myocytes. Cells were then treated with blebbistatin (10 µM) to preserve morphology and permeabilized in 0.1% Triton-X 100 PBS for five minutes. Cells were washed three times and fixed with 4% paraformaldehyde for 15 minutes. Coverslips were mounted onto glass slides and imaged on a Zeiss Axioskop LSM 510 laser scanning confocal microscope. No DNA served as a control. Images shown are at 40× with a blowup in the final panel.

Statistics

All results are expressed as mean±SEM. Multi-group comparisons were assessed using one way analysis of variance (ANOVA) with Bonnferoni post-hoc test with $P<0.05$ considered statistically different.

Results are shown in FIGS. 8-11 and FIGS. 15-20.

Example 3

Affinity between phospholamban and either RNA, L-DNA, or 2'-O-methyl DNA was determined as described in Example 1, except for the substitution of alternative xNAs for the ssDNA, as follows: RNA 5 mer, RNA 10 mer, RNA 20 mer, RNA 35 mer, RNA 50 mer, L-DNA 50 mer, and O-methyl DNA 50 mer. Each xNA was a mixture of 5'-FAM-labeled random sequences of the indicated length. Results are shown in FIG. 12A and FIG. 12B.

The SERCA activity exhibited in the presence of RNAs of random sequence and varying length was assayed as described in Example 1, except for the substitution of RNA 5 mer, RNA 20 mer, RNA 35 mer, or RNA 50-mer for ssDNA. Results are shown in FIG. 13.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

```
                                        SEQ ID NO: 1
GCTTG

SEQ ID NO: 2
ATAGCTTGCA

SEQ ID NO: 3
AGTGATAGCT ATGGT

SEQ ID NO: 4
AGCAGCACAG AGGTCAGATG

SEQ ID NO: 5
ACTGAGCATG GGATAACCGT TCTCAGACTT

SEQ ID NO: 6
AGCAGCACAG AGGTCAGATG CAGGTAGGGT CCTATGCGTG
CTACCGTGAA

SEQ ID NO: 7
NNNNNNNNNN NNNNNNNNNN NNNNNNNNNN NNNNNNNNNN
NNNNNNNNNN NNNNNNNNNN NNNNNNNNNN NNNNNNNNNN

SEQ ID NO: 8
TTGGGGAGGG GCACTGGGCA GTGTAATTTA CGAAAGCGAG
TTGGGGAGGG GCACTGGGCA GTGTAATTTA CGAAAGCGAG

SEQ ID NO: 9
GTAGAGATTC GTATTTGGG GAGAAGCGGC CGGAAGCGGA
```

---

What is claimed is:

1. A method of treating cardiac disease, the method comprising:
    administering to a subject a composition comprising:
        an xNA molecule comprising at least six nucleotides, in an amount effective to increase the rate of myocyte relaxation, wherein a dissociation constant of the xNA molecule with phospholamban is less than 260 nM; and
        a pharmaceutically acceptable carrier.

2. A method comprising:
    evaluating the efficacy of treatment of cardiac disease, wherein the treatment comprises administering to a subject a composition comprising a first xNA molecule comprising a predetermined length in an amount effective to increase myocyte relaxation, wherein a dissociation constant of the first xNA molecule with phospholamban is less than 260 nM; and
    selecting a predetermined length of a second xNA molecule for at least one subsequent treatment, wherein the change comprises:
        the predetermined length of the second xNA molecule is shorter than the predetermined length of the first xNA if treatment with the first xNA results in more myocyte relaxation than is desired; or
        the predetermined length of the second xNA molecule is longer than the predetermined length of the first xNA if treatment with the first xNA results in less myocyte relaxation than is desired.

3. The method of claim 1 wherein the xNA molecule comprises a randomized nucleotide sequence.

4. The method of claim 2 wherein the xNA molecule comprises a randomized nucleotide sequence.

5. The method of claim 1 wherein the xNA molecule comprises a mixture of two or more sequences.

6. The method of claim 2 wherein the xNA molecule comprises a mixture of two or more sequences.

7. The method of claim 1 wherein the xNA molecule comprises a mixture of three or more sequences.

8. The method of claim 2 wherein the xNA molecule comprises a mixture of three or more sequences.

9. The method of claim 1 wherein the xNA molecule comprises a pool of randomized nucleotide sequences.

10. The method of claim 2 wherein the xNA molecule comprises a pool of randomized nucleotide sequences.

11. The method of claim 1 wherein the xNA molecule comprises at least ten nucleotides.

12. The method of claim 2 wherein the xNA molecule comprises at least ten nucleotides.

13. The method of claim 1 wherein the dissociation constant of the xNA molecule with phospholamban is less than 20 nM.

14. The method of claim 2 wherein the dissociation constant of the xNA molecule with phospholamban is less than 20 nM.

* * * * *

```
                              SEQUENCE LISTING

<160> NUMBER OF SEQ ID NOS: 9

<210> SEQ ID NO 1
<211> LENGTH: 5
<212> TYPE: DNA
<213> ORGANISM: artificial
<220> FEATURE:
<223> OTHER INFORMATION: single stranded DNA that binds cytoplasmic
      domain Ia of phospholamban (PLN)
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)

<400> SEQUENCE: 1 gcttg                                                                      5

<210> SEQ ID NO 2
<211> LENGTH: 10
<212> TYPE: DNA
<213> ORGANISM: artificial
<220> FEATURE:
<223> OTHER INFORMATION: single stranded DNA that binds cytoplasmic
      domain Ia of phospholamban (PLN)
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)

<400> SEQUENCE: 2
atagcttgca                                                                10

<210> SEQ ID NO 3
<211> LENGTH: 15
<212> TYPE: DNA
<213> ORGANISM: artificial
<220> FEATURE:
<223> OTHER INFORMATION: single stranded DNA that binds cytoplasmic
      domain Ia of phospholamban (PLN)
```

```
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)

<400> SEQUENCE: 3
agtgatagct atggt                                                        15

<210> SEQ ID NO 4
<211> LENGTH: 20
<212> TYPE: DNA
<213> ORGANISM: artificial
<220> FEATURE:
<223> OTHER INFORMATION: single stranded DNA that binds cytoplasmic
      domain Ia of phospholamban (PLN)
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)

<400> SEQUENCE: 4
agcagcacag aggtcagatg                                                   20

<210> SEQ ID NO 5
<211> LENGTH: 30
<212> TYPE: DNA
<213> ORGANISM: artificial
<220> FEATURE:
<223> OTHER INFORMATION: single stranded DNA that binds cytoplasmic
      domain Ia of phospholamban (PLN)
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)

<400> SEQUENCE: 5
actgagcatg ggataaccgt tctcagactt                                        30

<210> SEQ ID NO 6
<211> LENGTH: 50
<212> TYPE: DNA
<213> ORGANISM: artificial
<220> FEATURE:
<223> OTHER INFORMATION: single stranded DNA that binds cytoplasmic
      domain Ia of phospholamban (PLN)
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)

<400> SEQUENCE: 6
agcagcacag aggtcagatg caggtagggt cctatgcgtg ctaccgtgaa                  50

<210> SEQ ID NO 7
<211> LENGTH: 80
<212> TYPE: DNA
<213> ORGANISM: artificial
<220> FEATURE:
<223> OTHER INFORMATION: single stranded DNA that binds cytoplasmic
      domain Ia of phospholamban (PLN)
<220> FEATURE:
<221> NAME/KEY: misc_feature
<222> LOCATION: (1)..(1)
<223> OTHER INFORMATION: fluorescently labeled at the 5' end with
      carboxyfluorescein (FAM)
<220> FEATURE:
<221> NAME/KEY: misc_feature
```

```
<222> LOCATION: (1)..(80)
<223> OTHER INFORMATION: n is a, c, g, or t

<400> SEQUENCE: 7
nnnnnnnnnn nnnnnnnnnn nnnnnnnnnn nnnnnnnnnn nnnnnnnnnn nnnnnnnnnn      60
nnnnnnnnnn nnnnnnnnnn                                                  80

<210> SEQ ID NO 8
<211> LENGTH: 80
<212> TYPE: DNA
<213> ORGANISM: artificial
<220> FEATURE:
<223> OTHER INFORMATION: single stranded DNA that binds cytoplasmic
      domain Ia of phospholamban (PLN)

<400> SEQUENCE: 8
ttggggaggg gcactgggca gtgtaattta cgaaagcgag ttggggaggg gcactgggca      60
gtgtaattta cgaaagcgag                                                  80

<210> SEQ ID NO 9
<211> LENGTH: 40
<212> TYPE: DNA
<213> ORGANISM: artificial
<220> FEATURE:
<223> OTHER INFORMATION: single stranded DNA that binds cytoplasmic
      domain Ia of phospholamban (PLN)

<400> SEQUENCE: 9
gtagagattc gtattttggg gagaagcggc cggaagcgga                            40
```